US009603936B2

(12) United States Patent
Flamme et al.

(10) Patent No.: US 9,603,936 B2
(45) Date of Patent: *Mar. 28, 2017

(54) POLYETHYLENE GLYCOL BASED PRODRUG OF ADRENOMEDULLIN AND USE THEREOF

(71) Applicants: Bayer Intellectual Property GmbH, Monheim (DE); BAYER PHARMA AKTIENGESELLSCHAFT, Berlin (DE)

(72) Inventors: Ingo Flamme, Reichshof (DE); Johannes Köbberling, Neuss (DE); Hans-Georg Lerchen, Leverkusen (DE); Nils Griebenow, Dormagen (DE); Rudolf Schohe-Loop, Wuppertal (DE); Sven Wittrock, Wuppertal (DE); Maria Köllnberger, Velbert (DE); Frank Wunder, Wuppertal (DE); Gorden Redlich, Bochum (DE); Andreas Knorr, Erkrath (DE); Julie Marley, Merseyside (DE); Iain Pritchard, Merseyside (DE)

(73) Assignee: Bayer Intellectual Property GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,568

(22) PCT Filed: Oct. 30, 2012

(86) PCT No.: PCT/EP2012/071507
§ 371 (c)(1),
(2) Date: Apr. 30, 2014

(87) PCT Pub. No.: WO2013/064508
PCT Pub. Date: May 10, 2013

(65) Prior Publication Data
US 2014/0287984 A1 Sep. 25, 2014

(30) Foreign Application Priority Data
Nov. 3, 2011 (EP) .................................. 11187735

(51) Int. Cl.
*A61K 38/22* (2006.01)
*A61K 47/48* (2006.01)
*C07K 14/575* (2006.01)

(52) U.S. Cl.
CPC ........ *A61K 47/48023* (2013.01); *A61K 38/22* (2013.01); *A61K 47/48215* (2013.01); *C07K 14/575* (2013.01)

(58) Field of Classification Search
None
See application file for complete search history.

(56) References Cited

U.S. PATENT DOCUMENTS

| 4,812,590 | A | 3/1989 | Saari |
| 6,028,066 | A | 2/2000 | Unger |
| 2002/0037846 | A1 | 3/2002 | Cadieux |
| 2010/0111865 | A1* | 5/2010 | Tolleshaug et al. ........... 424/9.1 |

FOREIGN PATENT DOCUMENTS

| CA | 2567478 A1 | 12/2005 |
| EP | 0296811 A2 | 12/1988 |
| WO | 02/083180 A1 | 10/2002 |
| WO | 2004/019993 A1 | 3/2004 |
| WO | 2004/043493 A1 | 5/2004 |
| WO | 2005/099768 A2 | 10/2005 |
| WO | 2006/136586 A2 | 12/2006 |
| WO | 2008/138141 A1 | 11/2008 |
| WO | 2011/089214 A1 | 7/2011 |
| WO | 02/089789 A1 | 11/2012 |

OTHER PUBLICATIONS

Hinson, Joy et al; "Adrenomedullin, a multifunctional regulatory peptide." Endocrine Rev. (2000) 21(2) p. 138-167.*
Nagaya, Noritoshi and Kangawa, Kenji; "Adrenomedullin in the treatment of pulmonary hypertension." Peptides (2004) 25 p. 2013-2018.*
Chapman, Andrew P. et al, "Therapeutic antibody fragments with prolonged in vivo half lives." Nature Biotechnol. (1999) 17 p. 780-783.*
Shechter, Yoram et al, "Reversible pegylation of peptide yy3-36 prolongs its inhibition of food intake in mice." FEBS Lett. (2005) 579 p. 2439-2444.*
Dennes, T. Joseph et al, "High yield activation of scaffold polymer surfaces to attach cell adhesion molecules." J. Am. Chem. Soc. (2007) 129 p. 93-97.*
"Nomenclature and Symbolism for Amino Acids and Peptides", Pure & Appl. Chem., vol. 56, No. 5, 1984, pp. 595-624.
Alberico, Dino et al., "Palladium-catalyzed sequential alkylation-alkenylation reactions: application towards the synthesis of polyfunctionalized fused aromatic rings", Tetrahedron, 61, 2005, pp. 6283-6297.
Caliceti, Paolo et al., "Pharmacokinetic and biodistribution properties of poly(ethylene glycol)-protein conjugates", Advanced Drug Delivery Reviews, vol. 55, Jan. 2003, pp. 1261-1277.
Chapman, Andrew P. et al., "Therapeutic antibody fragments with prolonged in vivo half-lifes", Nature Biotechnology, vol. 17, Aug. 1999, pp. 780-783.

(Continued)

*Primary Examiner* — Maury Audet
*Assistant Examiner* — Fred Reynolds
(74) *Attorney, Agent, or Firm* — Aseem Mehta

(57) ABSTRACT

The invention relates to novel polyethylene glycol (PEG) based prodrug of Adrenomedullin, to processes for preparation thereof, to the use thereof for treatment and/or prevention of diseases, and to the use thereof for producing medicaments for treatment and/or prevention of diseases, especially of cardiovascular, edematous and/or inflammatory disorders.

9 Claims, 1 Drawing Sheet

(56) References Cited

OTHER PUBLICATIONS

Figure 1:
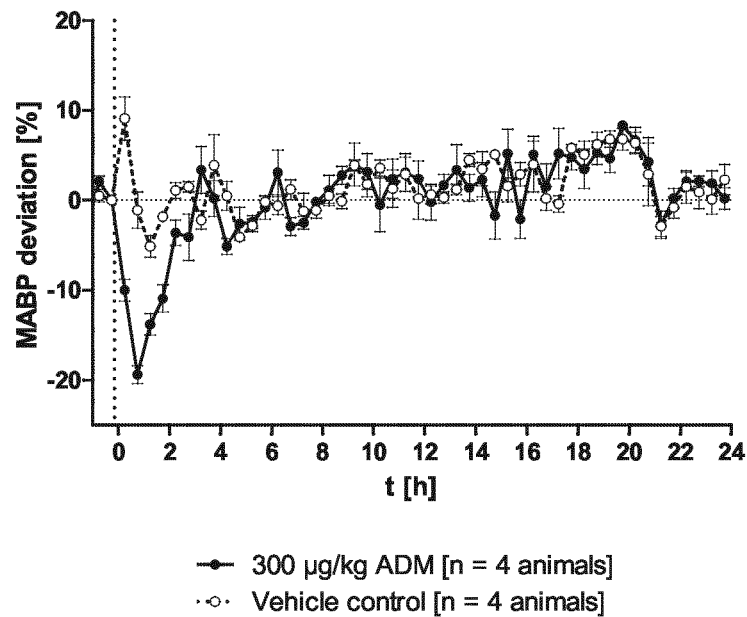

Dennes, T. Joseph et al., "High-Yield Activation of Scaffold Polymer Surfaces to Attach Cell Adhesion Molecules", J. Am. Chem. Soc., 129, 2007, pp. 93-97.
European Patent Office, International Search Report for International Patent Application No. PCT/EP2012/071507, Feb. 28, 2013, 4 pages.
European Patent Office, Written Opinion for International Patent Application No. PCT/EP2012/071507, May 3, 2014, 5 pages.
Garcia, Mario A. et al., "Adrenomedullin: a new and promising target for drug discovery", Expert Opin. Ther. Targets, 10(2), 2006, pp. 303-317.
Gibbons, Carrie et al., "Receptor Activity-Modifying Proteins: RAMPing up Adrenomedullin Signaling", Molecular Endocrinology 21(4), 2007, pp. 783-796.
Greenwald, Richard B. et al., "A New Aliphatic Amino Prodrug System for Delivery of Small Molecules and Proteins Utilizing Novel PEG Derivatives", Journal of Medical Chemistry, 47, 2004, pp. 726-734.
Greenwald, Richard B. et al., "Drug Delivery Systems Employing 1,4- or 1,6-Elimination: Poly(ethylene glycol) Prodrugs of Amine-Containing Compounds", J. Med. Chem., 42, 1999, pp. 3657-3667.
Hinson, Joy P. et al., "Adrenomedullin, a Multifunctional Regulatory Peptide", Endocrine Reviews, 21(2), 2000, pp. 138-167.
International Bureau of WIPO, International Preliminary Report on Patentability for International Patent Application No. PCT/EP2012/071507, May 6, 2014, 6 pages.
Kataoka, Yu et al., "The First Clinical Pilot Study of Intravenous Adrenomedullin Administration in Patients with Acute Myocardial Infarction", J. Cardiovasc Pharmacol, 56(4), 2010, pp. 413-419.
Murakami, Shinsuke et al., "Adrenomedullin Regenerates Alveoli and Vasculature in Elastase-induced Pulmonary Emphysema in Mice", American Journal Respir. Crit. Care Med., vol. 172, 2005, pp. 581-589.
Na, Dong H. et al., "Monitoring of peptide acylation inside degrading PLGA microspheres by capillary electrophoresis and MALDI-TOF mass spectrometry", Journal of Controlled Release 92, 2003, pp. 291-299.

Nagaya, Noritoshi et al., "Adrenomedullin in the treatment of pulmonary hypertension", Peptides, Elsevier, vol. 25, No. 11, Nov. 2004, pp. 2013-2018.
Peleg-Shulman, Tal et al., "Reversible PEGylation: a Novel Technology to Release Native Interferon a2 over a Prolonged Time Period", J. Med. Chem., 47, 2004, pp. 4897-4904.
Rautio, Jarkko et al., "Prodrugs: design and clinical applications", Nature Reviews, Drug Discovery, vol. 7, Mar. 2008, pp. 255-270.
Saari, Walfred S. et al., "Cyclization-Activated Prodrugs. Basic Carbamates of 4-Hydroxyanisole", Journal of Medical Chemistry, vol. 33, No. 1, 1990, pp. 97-101.
Shechter, Yoram et al., "Reversible PEGylation of peptide YY3-36 prolongs its inhibition of food intake in mice", FEBS Letters, 579, 2005, pp. 2439-2444.
Snider, Gordon L. et al., "Animal Models of Emphysema", American Review of Respiratory Disease, vol. 133, 1986, pp. 149-169.
Temmesfeld-Wollbruck, Bettina et al., "Adrenomedullin and endothelial barrier function", Thromb Haemost, 98, 2007, pp. 944-951.
Troughton, Richard W. et al., "Hemodynamic, Hormone, and Urinary Effects of Adrenomedullin Infusing in Essential Hypertension", Hypertension, 36(4), 2000, pp. 588-593.
Wang, Le Feng et al., "Role of Indicible Nitric Oxide Synthase in Pulmonary Microvascular Protein Leak in Murine Sepsis", Am. J. Respir. Crit. Care Med., vol. 165, 2002, pp. 1634-1639.
Wermuth, C.G. et al., "Glossary of Terms Used in Medical Chemistry", Pure & Appl. Chem., vol. 70, No. 5, 1998, pp. 1129-1143.
Wunder, Frank et al., "Pharmacological and Kinetic Characterization of Adrenomedullin 1 and Calcitonin Gene-Related Peptide 1 Receptor Reporter Cell Lines", Molecular Pharmacology, 73, 2008, pp. 1235-1243.
"Guatemala Oposition", Guatemala Application No. A-201400085, Nov. 16, 2015.
"IEPI Opposition", Ecuador Application No. SP-2014-133326, Mar. 6, 2015, 21.
"Index Merck 14th", Merck & Co., NJ. USA. 2006. No. 000175, 2006.
M. Westphal, et al., "Adrenomedullin: a smart road from pheochromocytoma to treatment of pulmonary hypertension", Eur Respir J 2004: 24: 518-520, 2004.

* cited by examiner

—●— 300 µg/kg ADM [n = 4 animals]
··○·· Vehicle control [n = 4 animals]

—●— 150 µg/kg Example 1 [n = 6 animals]
··○·· Vehicle control [n = 6 animals]

POLYETHYLENE GLYCOL BASED PRODRUG OF ADRENOMEDULLIN AND USE THEREOF

The invention relates to novel polyethylene glycol (PEG) based prodrug of Adrenomedullin, to processes for preparation thereof, to the use thereof for treatment and/or prevention of diseases, and to the use thereof for producing medicaments for treatment and/or prevention of diseases, especially of cardiovascular, edematous and/or inflammatory disorders.

The 52 amino acid peptide hormone adrenomedullin (ADM) is produced in adrenal gland, lung, kidney, heart muscle and other organs. The plasma levels of ADM are in the lower picomolar range. ADM is a member of the calcitonin gene-related peptide (CGRP) family of peptides and as such binds to a heterodimeric G-protein coupled receptor that consists of CRLR and RAMP 2 or 3 (Calcitonin-receptor-like receptor and receptor activity modifying protein 2 or 3). Activation of the ADM receptor leads to intracellular elevation of adenosine 3',5'-cyclic monophosphate (cAMP) in the receptor-bearing cells. ADM receptors are present on different cell types in almost all organs including endothelial cells. ADM is thought to be metabolized by neutral endopeptidase and is predominantly cleared in the lung where ADM-receptors are highly expressed [for review see Gibbons C., Dackor R., Dunworth W., Fritz-Six K., Caron K. M., *Mol Endocrinol* 21(4), 783-796 (2007)].

Experimental data from the literature suggest that ADM is involved in a variety of functional roles that include, among others, blood pressure regulation, bronchodilatation, renal function, hormone secretion, cell growth, differentiation, neurotransmission, and modulation of the immune response. Moreover ADM plays a crucial role as autocrine factor during proliferation and regeneration of endothelial cells [for review see Garcí a M. A., Martín-Santamarí a S., de Pascual-Teresa B., Ramos A., Julián M., Martínez A., *Expert Opin Ther Targets*, 10(2), 303-317 (2006)]

There is an extensive body of evidence from the literature which shows that ADM is indispensable for an intact endothelial barrier function and that administration of ADM to supra-physiological levels exerts strong anti-edematous and anti-inflammatory functions in a variety of inflammatory conditions in animal experiments including sepsis, acute lung injury and inflammation of the intestine [for review see Temmesfeld-Wollbrück B., Hocke A. C., Suttorp N., Hippenstiel S., *Thromb Haemost;* 98, 944-951 (2007)]

Clinical testing of ADM was so far conducted in cardiovascular indications with a measurable hemodynamic end point such as pulmonary hypertension, hypertension, heart failure and acute myocardial infarction. ADM showed hemodynamic effects in several studies in patients suffering from the aforementioned conditions. However, effects were only short lasting and immediately ceasing after the end of administration. This findings correlated well with the known pharmacokinetic profile of ADM. Pharmacodynamic effects comprised among others lowering of systemic and pulmonary arterial blood pressure and increase of cardiac output [Troughton R. W., Lewis L. K., Yandle T. G., Richards A. M., Nicholls M. G., *Hypertension,* 36(4), 588-93 (2000); Nagaya N., Kangawa K., *Peptides,* 25(11), 2013-8 (2004); Kataoka Y., Miyazaki S., Yasuda S., Nagaya N., Noguchi T., Yamada N., Morii I., Kawamura A., Doi K., Miyatake K., Tomoike H., Kangawa K., *J Cardiovasc Pharmacol,* 56(4), 413-9 (2010)]

In summary, based on evidence from a wealth of experimental data in animals and first clinical trials in man elevation of ADM to supraphysiological levels might be considered as a target mechanism for the treatment of a variety of disease conditions in man and animals. However, the major limitations of the use of ADM as therapeutic agent are the inconvenient applicability of continuous infusion therapy which precludes its use for most of the potential indications and the potentially limited safety margins with respect to hypotension which may result from bolus administrations of ADM.

The object of the present invention is to provide novel compounds which can be employed for the treatment of diseases, in particular cardiovascular, edematous and inflammatory disorders.

Many therapeutically active peptides or proteins suffer from high clearance in vivo. Several approaches to form an injectable depot of such drugs exist that involve the use of macromolecules.

Polymer matrices that contain a drug molecule in a non covalently bound state are well known. These can also be injectable as hydro gels, micro particles or micelles. The release kinetics of such drug products can be quite unreliable with high inter patient variability. Production of such polymers can harm the sensitive drug substance or it can undergo side reactions with the polymer during its degradation (D. H. Lee et al., J. Contr. Rel., 2003, 92, 291-299).

Permanent PEGylation of peptides or proteins to enhance their solubility, reduce immunogenicity and increase half live by reducing renal clearance is a well known concept since early 1980s (Caliceti P., Veronese F. M., Adv. Drug Deliv. Rev. 2003, 55, 1261-1277). For several drugs this has been used with success, but with many examples the PEGylation reduces efficacy of drug substance to an extent that this concept is not suitable any more (T. Peleg-Shulman et al., J. Med. Chem., 2004, 47, 4897-4904).

A suitable alternative are polymer based prodrugs. The current definitions for prodrugs by the IUPAC state the following terms (International Union of Pure and Applied Chemistry and International Union of Biochemistry: GLOSSARY OF TERMS USED IN MEDICINAL CHEMISTRY (Recommendations 1998); in Pure & Appl. Chem. Vol 70, No. 5, 1998, p. 1129-1143):

Prodrug: A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.

Carrier-linked prodrug (Carrier prodrug): A carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

Cascade prodrug: A cascade prodrug is a prodrug for which the cleavage of the carrier group becomes effective only after unmasking an activating group.

Several examples of PEG-based carrier prodrugs exist, most of them with the need for enzymatic activation of the linker between the active drug and the carrier, mostly initiated by enzymatic hydrolysis. Since esters are cleaved very readily and unpredictably in vivo, direct ester linkers for carrier pro drug have limitations to their usability (J. Rautio et al., Nature Reviews Drug discovery, 2008, 7 255-270).

Commonly used alternative approaches are cascading linkers attached to an amine functionality in the peptide or protein. In cascading linkers a masking group has to be removed as the rate limiting step in the cascade. This activates the linker to decompose in a second position to release the peptide or protein. Commonly the masking group can be removed by an enzymatic mechanism (R. B. Greenwald et al. in WO2002/089789, Greenwald, et al., J. Med. Chem. 1999, 42, 3657-3667, F. M. H. DeGroot et al. in WO2002/083180 and WO2004/043493, and D. Shabat et al. in WO2004/019993).

An alternative not relying on enzymatic activation is the concept of U. Hersel et al. in WO2005/099768. In their approach the masking group on a phenol is removed in a purely pH dependent manner by the attack of an internal nucleophile. This activates the linker for further decomposition.

As mentioned by U. Hersel et al. in WO2005/099768, "The disadvantage in the above-mentioned prodrug systems described by Greenwald, DeGroot and Shabat is the release of potentially toxic aromatic small molecule side products like quinone methides after cleavage of the temporary linkage. The potentially toxic entities are released in a 1:1 stoichiometry with the drug and can assume high in vivo concentrations." The same problem holds true for the system by Hersel et al. as well.

For small organic molecules a plethora of different prodrug approaches exist D. Rautio et al., Nature Reviews Drug discovery, 2008, 7 255-270). The approach used by U. Hersel et al. as release mechanism for their masking group has been used as a prodrug approach for phenolic groups of small molecules since the late 1980s. (W. S. Saari in EP 0296 811 and W. S. Saari et al., J. Med. Chem. 1990, Vol 33, No 1, p 97-101).

Alternative amine based prodrug system are based on the slow hydrolysis of bis-hydroxyethyl glycine as a cascading prodrug. The hydroxy groups of the bis-hydroxyethyl glycine are masked by esters that are prone to hydrolysis by esterases (R. Greenwald et al., J. Med. Chem. 2004, 47, 726-734 and D. Vetter et al. in WO 2006/136586).

Labeled Adrenomedullin derivatives for use as imaging and also therapeutic agent are known (J. Depuis et al. in CA 2567478 and WO 2008/138141). In these ADM derivatives a complexating cage like molecular structure capable of binding radioactive isotopes was attached to the N terminus of ADM in a direct manner or via a spacer unit potentially also including short PEG spacers. The diagnostic or therapeutic value of theses drugs arises from the targeted delivery of the radioactive molecule.

In contrast to the prodrug approaches listed above, which are all based on masking amine functionalities, the current invention is based on masking the phenolic group of a tyrosine in ADM. A carrier-linked prodrug is used, based on the internal nucleophile assisted cleavage of a carbamate on this phenolic group. The key advantage to other prodrug classes mentioned above is the toxicological harmlessness of the linker decomposition product, a cyclic urea permanently attached to the carrier. Furthermore, the decomposition of the prodrug is not dependent on enzymatic mechanisms that might cause a high inter patient variability of cleavage kinetics. The cleavage mechanism is solely pH dependent as an internal amine that is protonated at acidic pH gets activated at higher (neutral) pH to act as a nucleophile attacking the phenolic carbamate based on the tyrosine.

In the context of the present invention, compounds are now described which act as slow release ADM-prodrugs with extended duration of pharmacological action as compared to ADM and which on the basis of this specific action mechanism—after parenteral administration—exert in vivo sustained anti-inflammatory and hemodynamic effects such as stabilization of endothelial barrier function, and reduction of blood pressure, respectively.

The present invention provides compounds of the formula

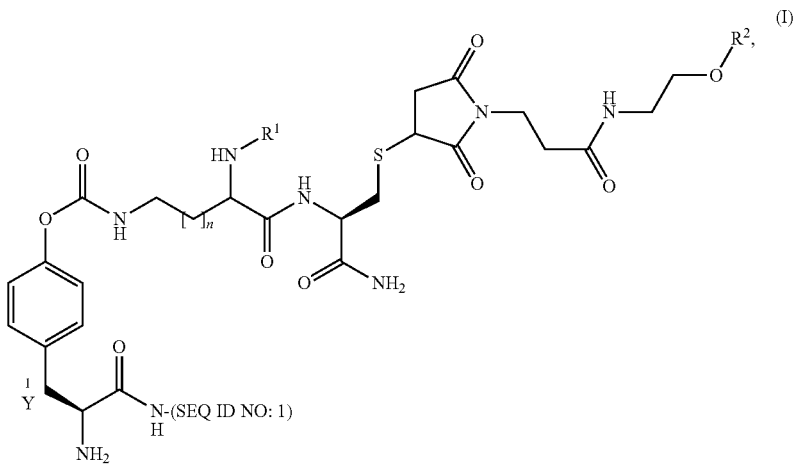

in which
n represents the number 0, 1, 2 or 3,
$R^1$ represents hydrogen, methyl, ethyl, n-propyl or iso-propyl,
$R^2$ represents linear or branched PEG 20 kDa to 80 kDa endcapped with a methoxy-group,
and salts thereof, solvates thereof and the solvates of salts thereof.

Compounds according to the invention are the compounds of the formula (I) and the salts thereof, solvates thereof and solvates of the salts thereof, the compounds which are embraced by formula (I) and are of the formulae specified below and the salts thereof, solvates thereof and solvates of the salts thereof, and the compounds which are embraced by formula (I) and are specified below as working examples and salts thereof, solvates thereof and solvates of the salts thereof, if the compounds which are embraced by formula (I) and are specified below are not already salts, solvates and solvates of the salts.

Depending on their structure, the compounds according to the invention may exist in stereoisomeric forms (enantiomers, diastereomers). The invention therefore embraces the enantiomers or diastereomers and the particular mixtures thereof. The stereoisomerically homogeneous constituents can be isolated in a known manner from such mixtures of enantiomers and/or diastereomers.

When the compounds according to the invention can occur in tautomeric forms, the present invention embraces all tautomeric forms.

In the context of the present invention, preferred salts are physiologically acceptable salts of the compounds according to the invention. Also included are salts which are not suitable themselves for pharmaceutical applications, but, for example, can be used for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, maleic acid, citric acid, fumaric acid, maleic acid and benzoic acid.

Physiologically acceptable salts of the compounds according to the invention also include salts of customary bases, for example and with preference alkali metal salts (e.g. sodium and potassium salts), alkaline earth metal salts (e.g. calcium and magnesium salts) and ammonium salts derived from ammonia or organic amines having 1 to 16 carbon atoms, for example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of the solvates, in which the coordination is with water. Preferred solvates in the context of the present invention are hydrates.

In the context of the invention endcapped with a methoxy-group mentioned in $R^2$ means that the polyethylene glycol (PEG) is substituted with a methoxy group at the end which is not bond to the oxygen, i.e.—PEG 40 kDa-OMe.

Preference is given to compounds of the formula (I) in which
n represents the number 1 or 2,
$R^1$ represents hydrogen or methyl,
$R^2$ represents linear PEG 40 kDa endcapped with a methoxy-group.

Preference is also given to compounds of the formula (I) in which
n represents the number 1 or 2,
$R^1$ represents hydrogen,
$R^2$ represents linear PEG 40 kDa endcapped with a methoxy-group.

Preference is also given to compounds of the formula (I) in which n represents the number 1.

Preference is also given to compounds of the formula (I) in which $R^1$ represents hydrogen.

Preference is also given to compounds of the formula (I) in which the carbon atom to which the —$NHR^1$ substituent is bonded has S configuration.

Preference is also given to compounds of the formula (I) in which $R^2$ represents linear PEG 40 kDa endcapped with a methoxy-group.

Preference is also given to compounds of the formula (I) which have the structure of the formula (Ia)

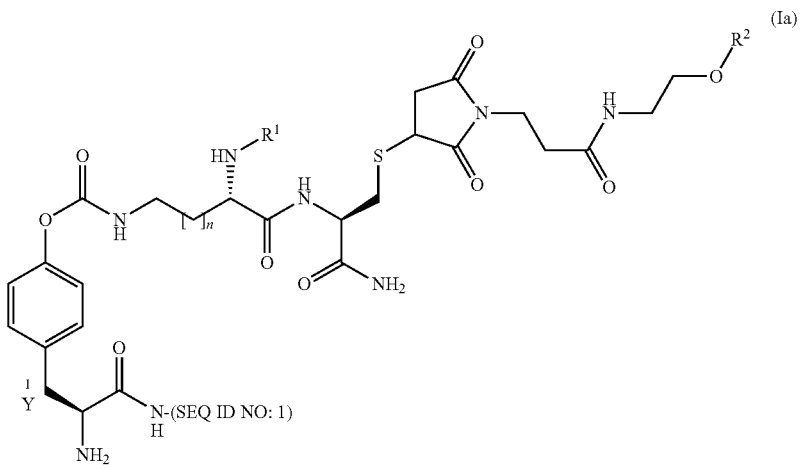

in which
n, $R^1$ and $R^2$ are each as defined above,
and salts thereof, solvates thereof and the solvates of salts thereof.

The specific radical definitions given in the particular combinations or preferred combinations of radicals are, irrespective of the particular combination of the radical specified, also replaced by any radical definitions of other combinations.

Very particular preference is given to combinations of two or more of the above-mentioned preferred ranges.

The invention further provides a process for preparing the compounds of the formula (I), or salts thereof, solvates thereof or the solvates of salts thereof, wherein the compounds of the formula (II)

(II)

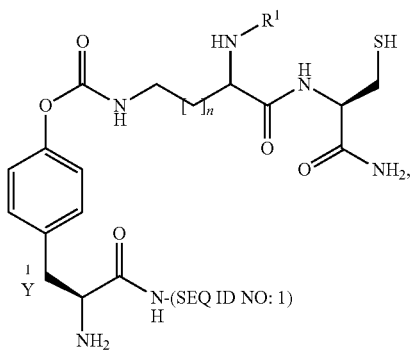

in which
n and R¹ are each as defined above,
are reacted with the compounds of the formula (III)

(III)

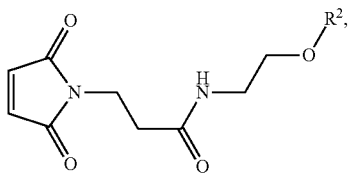

in which
R² is as defined above.

The reaction is generally effected in inert solvents, preferably in a temperature range of 0° C. to 50° C. at standard pressure.

Inert solvents are, for example, citrate buffers, glycine-hydrochloride buffers, phthalate buffers or acetate buffers of pH 3 to 5, preference being given to a citrate buffer of pH 4.

The compound of the formula (III) is known or can be synthesized by known processes from the appropriate starting compounds.

The compounds of the formula (II) are known or can be prepared by reacting compounds of the formula (IV)

(IV)

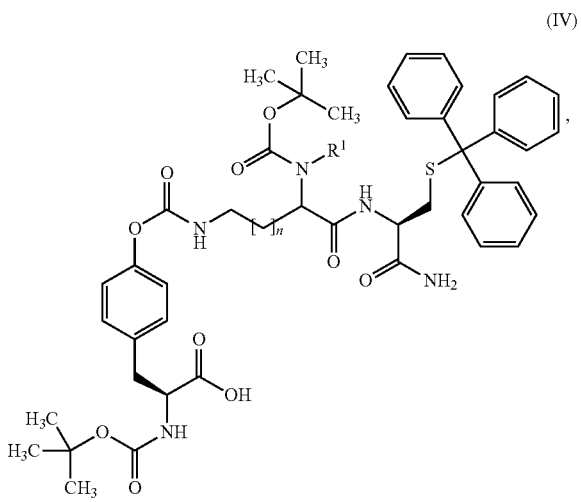

in which
n and R¹ are each as defined above,
in the first stage with the compound of the formula (V)

(V)

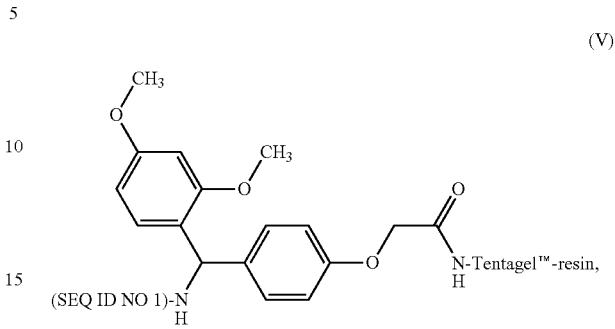

and in the second stage with an acid.

The reaction in the first stage is generally effected in inert solvents, in the presence of a dehydrating reagent, optionally in the presence of a base, preferably in a temperature range from room temperature to 70° C. at standard pressure.

Inert solvents are, for example, halohydrocarbons such as dichloromethane, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to dimethylformamide.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylamino-isopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxy-carbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), benzotriazol-1-yl-N-tetramethyl-uronium tetrafluoroborate (TBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PYBOP), or N-hydroxysuccinimide, or mixtures of these with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or N,N-diisopropylethylamine, preference being given to N,N-diisopropylethylamine.

Preferably, the condensation is carried out with TBTU in the presence of N,N-diisopropylethylamine.

The second stage reaction is optionally effected in inert solvents, preferably in a temperature range from room temperature to 60° C. at standard pressure.

Inert solvents are, for example, halohydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to concentrated trifluoroacetic acid. Concentrated trifluoroacetic acid can be used with addition of scavengers like water, phenol, thioanisole and 1,2-ethanediol. Preference is given to 1 to 5% of each of these scavengers.

The compound of the formula (V) is known or can be synthesized by known processes from the appropriate starting compounds (example 14A).

The compounds of the formula (IV) are known or can be prepared by reacting compounds of the formula (VI)

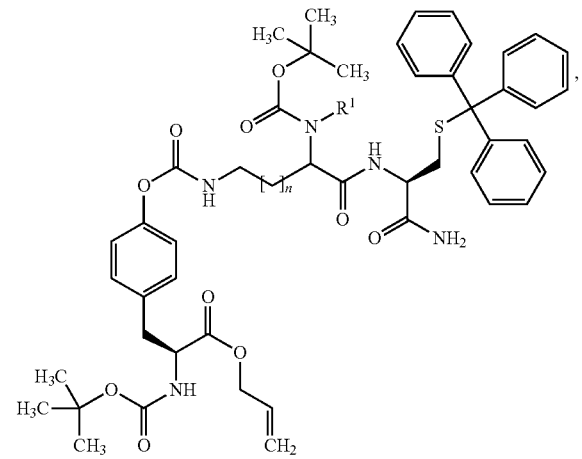

(VI)

in which n and $R^1$ are each as defined above, with a Palladium(0) source and a reducing agent.

The reaction is generally effected in inert solvents, optionally in the presents of a weak base, preferably in a temperature range of 0° C. to 50° C. at standard pressure.

Inert solvents are, for example, halohydrocarbons such as dichloromethane, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to tetrahydrofuran.

Palladium(0) sources are, for example, tetrakis(triphenylphosphin)palladium(0), tris(dibenzylideneacetone)dipalladium(0) or Palladium(II) sources that are reduced in situ to Palladium(0) during the reaction, preference being given to tetrakis(triphenylphosphin)-palladium(0).

Reducing agents are, for example, formic acid or triethyl silan, preference being given to formic acid.

Bases are, for example, triethylamine, N,N-diisopropylethylamine or potassium phosphate solution, preference being given to triethylamine.

The compounds of the formula (VI) are known or can be prepared by reacting compounds of the formula (VII)

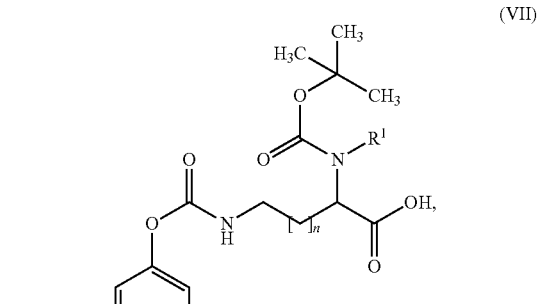

(VII)

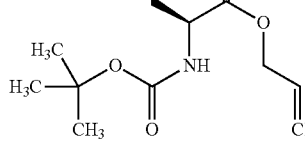

in which n and $R^1$ are each as defined above, with the compound of the formula (VIII)

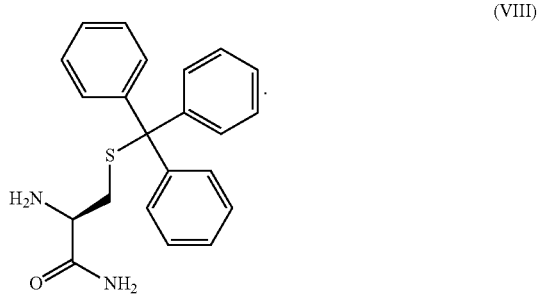 [SMILES: NC(=O)[C@@H](N)CSC(c1ccccc1)(c1ccccc1)c1ccccc1]

(VIII)

The reaction is generally effected in inert solvents, in the presence of a dehydrating reagent, optionally in the presence of a base, preferably in a temperature range from room temperature to 70° C. at standard pressure.

Inert solvents are, for example, halohydrocarbons such as dichloromethane, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to dichloromethane.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxy-carbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), benzotriazol-1-yl-N-tetramethyl-uronium tetrafluoroborate (TBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PYBOP), or N-hydroxysuccinimide, or mixtures of these with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or N,N-diisopropylethylamine, preference being given to N,N-diisopropylethylamine.

Preferably, the condensation is carried out with HATU in the presence of N,N-diisopropylethylamine.

The compounds of the formula (VII) and (VIII) are known or can be synthesized by known processes from the appropriate starting compounds.

The preparation of the compounds according to the invention can be illustrated by the following synthesis scheme:

Scheme 1
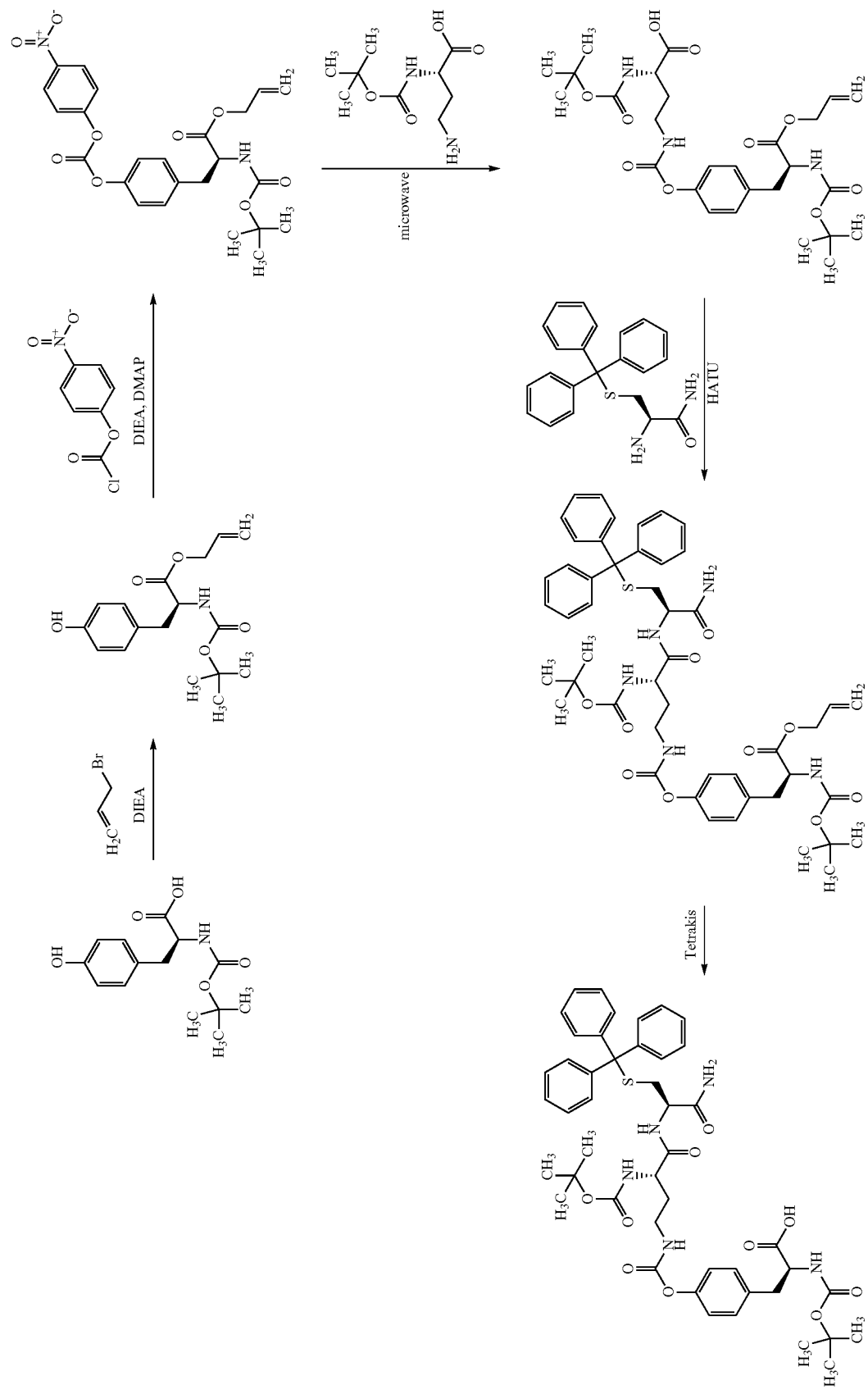

The compounds according to the invention show an unforeseeable useful spectrum of pharmacological activity.

Accordingly they are suitable for use as medicaments for treatment and/or prevention of diseases in humans and animals.

The compounds according to the invention are distinguished as specific adrenomedullin (ADM) releasing prodrugs.

The present invention further provides for the use of the compounds according to the invention for treatment and/or prevention of disorders, especially of cardiovascular, edematous and/or inflammatory disorders.

For the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing, a disease, disorder, condition, or state, the development and/or progression thereof, and/or the symptoms thereof. The term prevention includes prophylaxis. Treatment or prevention of a disease, disorder, condition, or state may be partial or complete.

On the basis of their pharmacological properties, the compounds according to the invention can be employed for treatment and/or prevention of cardiovascular diseases, in particular heart failure, especially chronic and acute heart failure, diastolic and systolic (congestive) heart failure, acute decompensated heart failure, cardiac insufficiency, coronary heart disease, angina pectoris, myocardial infarction, ischemia reperfusion injury, ischemic and hemorrhagic stroke, arteriosclerosis, atherosclerosis, hypertension, especially essential hypertension, malignant essential hypertension, secondary hypertension, renovascular hypertension and hypertension secondary to renal and endocrine disorders, hypertensive heart disease, hypertensive renal disease, pulmonary hypertension, especially secondary pulmonary hypertension, pulmonary hypertension following pulmonary embolism with and without acute cor pulmonale, primary pulmonary hypertension, and peripheral arterial occlusive disease.

The compounds according to the invention are furthermore suitable for treatment and/or prevention of gestational [pregnancy-induced] edema and proteinuria with and without hypertension (pre-eclampsia).

The compounds according to the invention are furthermore suitable for treatment and/or prevention of pulmonary disorders, such as chronic obstructive pulmonary disease, asthma, acute and chronic pulmonary edema, allergic alveolitis and pneumonitis due to inhaled organic dust and particles of fungal, actinomycetic or other origin, acute chemical bronchitis, acute and chronic chemical pulmonary edema (e.g. after inhalation of phosgene, nitrogen oxide), neurogenic pulmonary edema, acute and chronic pulmonary manifestations due to radiation, acute and chronic interstitial lung disorders (such as but not restricted to drug-induced interstitial lung disorders, e.g. secondary to Bleomycin treatment), acute lung injury/acute respiratory distress syndrome (ALI/ARDS) in adult or child including newborn, ALI/ARDS secondary to pneumonia and sepsis, aspiration pneumonia and ALI/ARDS secondary to aspiration (such as but not restricted to aspiration pneumonia due to regurgitated gastric content), ALI/ARDS secondary to smoke gas inhalation, transfusion-related acute lung injury (TRALI), ALI/ARDS or acute pulmonary insufficiency following surgery, trauma or burns, ventilator induced lung injury (VILI), lung injury following meconium aspiration, pulmonary fibrosis, and mountain sickness.

The compounds according to the invention are furthermore suitable for treatment and/or prevention of chronic kidney diseases (stages 1-5), renal insufficiency, diabetic nephropathy, hypertensive chronic kidney disease, glomerulonephritis, rapidly progressive and chronic nephritic syndrome, unspecific nephritic syndrome, nephrotic syndrome, hereditary nephropathies, acute and chronic tubulo-interstitial nephritis, acute kidney injury, acute kidney failure, posttraumatic kidney failure, traumatic and postprocedural kidney injury, cardiorenal syndrome, and protection and functional improvement of kidney transplants.

The compounds are moreover suitable for treatment and/or prevention of diabetes mellitus and its consecutive symptoms, such as e.g. diabetic macro- and microangiopathy, diabetic nephropathy and neuropathy.

The compounds according to the invention can moreover be used for treatment and/or prevention of disorders of the central and peripheral nervous system such as viral and bacterial meningitis and encephalitis (e.g. Zoster encephalitis), brain injury, primary or secondary [metastasis] malignant neoplasm of the brain and spinal cord, radiculitis and polyradiculitis, Guillain-Barre syndrome [acute (post-)infective polyneuritis, Miller Fisher Syndrome], amyotrophic lateral sclerosis [progressive spinal muscle atrophy], Parkinson's disease, acute and chronic polyneuropathies, pain, cerebral edema, Alzheimer's disease, degenerative diseases of the nervous system and demyelinating diseases of the central nervous system such as but not restricted to multiple sclerosis.

The compounds according to the invention are furthermore suitable for treatment and/or prevention of portal hypertension and liver fibrosis [cirrhosis] and its sequelae such as esophageal varices and ascites, for the treatment and/or prevention of pleural effusions secondary to malignancies or inflammations and for the treatment and/or prevention of lymphedema and of edema secondary to varices.

The compounds according to the invention are furthermore suitable for treatment and/or prevention of inflammatory disorders of the gastrointestinal tract such as inflammatory bowel disease, Crohn's disease, ulcerative colitis, and toxic and vascular disorders of the intestine.

The compounds according to the invention are furthermore suitable for treatment and/or prevention of sepsis, septic shock, systemic inflammatory response syndrome (SIRS) of non-infectious origin, hemorrhagic shock, sepsis or SIRS with organ dysfunction or multi organ failure (MOF), traumatic shock, toxic shock, anaphylactic shock, urticaria, insect sting and bite-related allergies, angioneurotic edema [Giant urticaria, Quincke's edema], acute laryngitis and tracheitis, and acute obstructive laryngitis [croup] and epiglottitis.

The compounds are furthermore suitable for treatment and/or prevention of diseases of the rheumatic type and other disease forms to be counted as autoimmune diseases such as but not restricted to polyarthritis, lupus erythematodes, scleroderma, purpura and vasculitis.

The compounds according to the invention are furthermore suitable for treatment of ocular hypertension (glaucoma), diabetic retinopathy and macular edema.

The compounds according to the invention can moreover be used for treatment and/or prevention of operation-related states of ischemia and consecutive symptoms thereof after surgical interventions, in particular interventions on the heart using a heart-lung machine (e.g. bypass operations, heart valve implants), interventions on the carotid arteries, interventions on the aorta and interventions with instrumental opening or penetration of the skull cap.

The compounds are furthermore suitable for general treatment and/or prevention in the event of surgical interventions with the aim of accelerating wound healing and shortening the reconvalescence time. They are further suited for the promotion of wound healing.

The compounds are furthermore suitable for treatment and/or prevention of disorders of bone density and structure such as but not restricted to osteoporosis, osteomalacia and hyperparathyroidism-related bone disorders.

The compounds are furthermore suitable for treatment and/or prevention of sexual dysfunctions, in particular male erectile dysfunction.

Preferable the compounds are suitable for treatment and/or prevention of heart failure, coronary heart disease, ischemic and/or hemorrhagic stroke, hypertension, pulmonary hypertension, peripheral arterial occlusive disease, pre-eclampsia, chronic obstructive pulmonary disease, asthma, acute and/or chronic pulmonary edema, allergic alveolitis and/or pneumonitis due to inhaled organic dust and particles of fungal, actinomycetic or other origin, and/or acute chemical bronchitis, acute and/or chronic chemical pulmonary edema, neurogenic pulmonary edema, acute and/or chronic pulmonary manifestations due to radiation, acute and/or chronic interstitial lung disorders, acute lung injury/acute respiratory distress syndrome (ALI/ARDS) in adult or child including newborn, ALI/ARDS secondary to pneumonia and sepsis, aspiration pneumonia and ALI/ARDS secondary to aspiration, ALI/ARDS secondary to smoke gas inhalation, transfusion-related acute lung injury (TRALI), ALI/ARDS and/or acute pulmonary insufficiency following surgery, trauma and/or burns, and/or ventilator induced lung injury (VILI), lung injury following meconium aspiration, pulmonary fibrosis, mountain sickness, chronic kidney diseases, glomerulonephritis, acute kidney injury, cardiorenal syndrome, lymphedema, inflammatory bowel disease, sepsis, septic shock, systemic inflammatory response syndrome (SIRS) of non-infectious origin, anaphylactic shock, inflammatory bowel disease and/or urticaria.

More preferable the compounds are suitable for treatment and/or prevention of heart failure, hypertension, pulmonary hypertension, asthma, acute and/or chronic chemical pulmonary edema, acute lung injury/acute respiratory distress syndrome (ALI/ARDS) in adult or child including newborn, ALI/ARDS secondary to pneumonia and sepsis, aspiration pneumonia and ALI/ARDS secondary to aspiration, ALI/ARDS secondary to smoke gas inhalation, transfusion-related acute lung injury (TRALI), ALI/ARDS and/or acute pulmonary insufficiency following surgery, trauma and/or burns, and/or ventilator induced lung injury (VILI), lung injury following meconium aspiration, sepsis, septic shock, systemic inflammatory response syndrome (SIRS) of non-infectious origin, anaphylactic shock, inflammatory bowel disease and/or urticaria.

The present invention further provides for the use of the compounds according to the invention for treatment and/or prevention of disorders, in particular the disorders mentioned above.

The present invention further provides for the use of the compounds according to the invention for preparing a medicament for treatment and/or prevention of disorders, in particular the disorders mentioned above.

The present invention further provides a method for treatment and/or prevention of disorders, in particular the disorders mentioned above, using an active amount of the compounds according to the invention.

The invention further provides medicaments comprising a compound according to the invention and one or more further active ingredients, in particular for treatment and/or prevention of the disorders mentioned above. Exemplary and preferred active ingredient combinations are:

ACE inhibitors, angiotensin receptor antagonists, beta-2 receptor agonists, phosphodiesterase inhibitors, glucocorticoid receptor agonists, diuretics, or recombinant angiotensin converting enzyme-2 or acetylsalicylic acid (aspirin).

In a preferred embodiment of the invention, the compounds according to the invention are administered in combination with an ACE inhibitor, such as, by way of example and preferably, enalapril, quinapril, captopril, lisinopril, ramipril, delapril, fosinopril, perindopril, cilazapril, imidapril, benazepril, moexipril, spirapril or trandopril.

In a preferred embodiment of the invention, the compounds according to the invention are administered in combination with an angiotensin receptor antagonist, such as, by way of example and preferably, losartan, candesartan, valsartan, telmisartan or embusartan.

In a preferred embodiment of the invention, the compounds according to the invention are administered in combination with a beta-2 receptor agonist, such as, by way of example and preferably, salbutamol, pirbuterol, salmeterol, terbutalin, fenoterol, tulobuterol, clenbuterol, reproterol or formoterol.

In a preferred embodiment of the invention, the compounds according to the invention are administered in combination with a phosphodiesterase (PDE) inhibitor, such as, by way of example and preferably, milrinone, aminone, pimobendan, cilostazol, sildenafil, vardenafil or tadalafil.

In a preferred embodiment of the invention, the compounds according to the invention are administered in combination with a glucocorticoid receptor agonist, such as, by way of example and preferably, cortiosol, cortisone, hydrocortisone, prednisone, methyl-prednisolone, prednylidene, deflazacort, fluocortolone, triamcinolone, dexamethasone or betamethasone.

In a preferred embodiment of the invention, the compounds according to the invention are administered in combination with diuretics, such as, by way of example and preferably, furosemide, torasemide and hydrochlorothiazide.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way, for example by the parenteral, pulmonary, nasal, sublingual, lingual, buccal, dermal, transdermal, conjunctival, optic route or as implant or stent.

The compounds according to the invention can be administered in administration forms suitable for these administration routes.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration include preparations for injection and infusion in the form of solutions, suspensions, emulsions, lyophilizates or sterile powders.

Suitable for the other administration routes are, for example, pharmaceutical forms for inhalation (including powder inhalers, nebulizers), nasal drops, eye drops, solutions or sprays; films/wafers or aqueous suspensions (lotions, shaking mixtures), lipophilic suspensions, ointments, creams, transdermal therapeutic systems (e.g. patches), milk, pastes, foams, dusting powders, implants or stents.

Parenteral administration is preferred, especially intravenous administration.

The compounds according to the invention can be converted into the stated administration forms. This can take place in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colors (e.g. inorganic pigments, for example iron oxides) and masking flavors and/or odors.

It has generally been found to be advantageous, in the case of parenteral administration, to administer amounts of about 0.001 to 5 mg/kg, preferably about 0.01 to 1 mg/kg, of body weight to achieve effective results.

It may nevertheless be necessary in some cases to deviate from the stated amounts, in particular as a function of the body weight, route of administration, individual response to the active ingredient, nature of the preparation and time or interval over which administration takes place. For instance, less than the aforementioned minimum amount may be sufficient in some cases, whereas in other cases the stated upper limit must be exceeded. In the case of administration of larger amounts, it may be advisable to divide these into a plurality of individual doses over the day.

The following working examples illustrate the invention. The invention is not restricted to the examples.

The percentages in the following tests and examples are, unless stated otherwise, percentages by weight; parts are parts by weight. Solvent ratios, dilution ratios and concentration data for the liquid/liquid solutions are each based on volume.

A. EXAMPLES

Abbreviations

AA amino acid
Acm acetamidomethyl
ADM adrenomedullin (human)
ADM (2-52) Peptide sequence of ADM AA 2 to AA 52, including disulfide bond and C-terminal amide
approx. approximately
Boc tert-butyloxycarbonyl
CDI carbonyldiimidazole
d day(s), doublet (in NMR)
TLC thin-layer chromatography
DCI direct chemical ionization (in MS)
dd doublet of doublets (in NMR)
DIEA N,N-diisopropylethylamine
DMAP 4-dimethylaminopyridine
DMF N,N-dimethylformamide
DMSO dimethyl sulfoxide
of theory of theory (in yield)
eq. equivalent(s)
ESI electrospray ionization (in MS)
Fmoc (9H-fluoren-9-ylmethoxy)carbonyl
h hour(s)
HATU O-(7-azabenzotriazol-1-yl)-N,N,N',N'-tetramethyluronium hexafluorophosphate
HPLC high pressure, high performance liquid chromatography
LC-MS liquid chromatography-coupled mass spectroscopy
m multiplet (in NMR)
min minute(s)
MS mass spectroscopy
NMR nuclear magnetic resonance spectroscopy
pbf 2,2,4,6,7-pentamethyldihydrobenzofuran-5-sulfonyl
PEG polyethylene glycol
RP reversed phase (in HPLC)
RT room temperature
$R_t$ retention time (in HPLC)
s singulet (in NMR)
TBTU benzotriazol-1-yl-N-tetramethyl-uronium tetrafluoroborate
tBu tert-butyl
TFA trifluoroacetic acid
THF tetrahydrofuran
Trt trityl Nomenclature of amino acids and peptide sequences is according to:

International Union of Pure and Applied Chemistry and International Union of Biochemistry: Nomenclature and Symbolism for Amino Acids and Peptides (Recommendations 1983). In: Pure & Appl. Chem. 56, Vol. 5, 1984, p. 595-624

| Trivial Name | Symbol | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

LC-MS and MS Methods

Method 1 (LC-MS):

Instrument type: Waters ACQUITY SQD UPLC System; column: Waters Acquity UPLC HSS T3 1.8µ 50 mm×1 mm; mobile phase A: 1 l water+0.25 ml 99% strength formic acid, mobile phase B: 1 l acetonitrile+0.25 ml 99% strength formic acid; gradient: 0.0 min 90% A→1.2 min 5% A→2.0 min 5% A; oven: 50° C.; flow: 0.40 ml/min; UV-detection: 210-400 nm.

Method 2 (LC-MS):

MS instrument: type: Waters (Micromass) Quattro Micro; HPLC instrument type: Agilent 1100 series; column: Thermo Hypersil GOLD 3µ 20 mm×4 mm; mobile phase A: 1 l water+0.5 ml 50% strength formic acid, mobile phase B: 1 l acetonitrile+0.5 ml 50% strength formic acid; gradient: 0.0 min 100% A→3.0 min 10% A→4.0 min 10% A; oven: 50° C.; flow: 2.0 ml/min; UV-detection: 210 nm.

Method 3 (HPLC):
Instrument type: HP 1200 Series; UV DAD; column: Phenomenex Luna 5 μm C5 100 Å, 150 mm×4.6 mm; mobile phase A: 1 l water+0.5 ml 50% strength formic acid, mobile phase B: 1 l acetonitrile+0.5 ml 50% strength formic acid; gradient: 0.0 min 95% A→5 min 5% A; →5.8 min 95% A→6.2 min 95% A; flow rate: 2.5 ml/min; oven: RT; UV detection: 210 nm.

Method 4 (HPLC):
Instrument type: HP 1200 Series; UV DAD; column: Merck Chromolith Fastgradient RP18 50 mm×2 mm; mobile phase A: 1 l water+0.5 ml 50% strength formic acid, mobile phase B: 1 l acetonitrile+0.5 ml 50% strength formic acid; gradient: 0.0 min 95% A→2.9 min 5% A→3.2 min 5% A; flow rate: 3 ml/min; oven: RT; UV detection: 210 nm.

Method 5 (DCI MS):
Instrument type: Thermo Fisher-Scientific DSQ; chemical ionization; reactant ammonia gas; source temperature: 200° C.; inonization energy 70 eV.

Method 6 (MALDI MS):
Instrument type Kratos PC-Kompact SEQ V1.2.2 MALDI TOF MS, positive ionization mode, Linear high, Power: 75.

Microwave Synthesizer:
Biotage Emrys Initiator II synthesizer, with variable vial size up to 20 ml reaction volume and "Robot 60" sample processor pH 4 Citrate Buffer:
Fluka No 82566; Citrate buffer pH 4, stabilized with sodium azide composition: citric acid, ~0.056 M; sodium azide, ~0.05%; sodium chloride, ~0.044 M; sodium hydroxide, ~0.068 M.

40 kDa methoxy poly(ethylene glycol) maleimido propionamide (linear 40k mPEG maleimide); CAS No 724722-89-8; From Dr. Reddys Inc., Lot No 233101301; Weight average molecular weight, Mw (GPC) 40500 Da; Polydispersity (GPC) 1.08.

Starting Compounds

Example 1A

Allyl-N-(tert-butoxycarbonyl)-O-[(4-nitrophenoxy)carbonyl]-L-tyrosinate

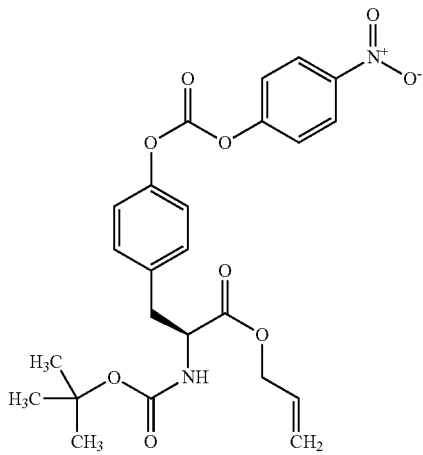 [SMILES: C=CCOC(=O)[C@H](Cc1ccc(OC(=O)Oc2ccc([N+](=O)[O-])cc2)cc1)NC(=O)OC(C)(C)C]

36.7 g (114.3 mmol) N-Boc-L-tyrosine allyl ester, 23.0 g (114.3 mmol) 4-nitrophenyl chloroformate, 17.5 ml (125.7 mmol) triethylamine and 1.40 g (11.4 mmol) 4-dimethylamino pyridine were combined in 1000 ml dichloromethane and stirred at room temperature for 2 h. The reaction mixture was extracted with approx. 500 ml water and with approx. 250 ml brine and dried over approx. 100 g sodium sulfate. The solvent was removed by rotary evaporation (approx. 40° C., approx. 200 mbar, approx. 30 min.) and the product was dissolved in warm diethyl ether and crystallized over night at 4° C. The crystals were filtered of, washed with cold diethyl ether and dried in high vacuum (approx. 0.1 mbar, 18 h). The yield was 29.86 g, (59.6 mmol, 52% of theory) of the desired product.

LC-MS (method 1): $R_t$=1.23 min, m/z=487 (M+H)$^+$

Example 2A (2S)-4-{[(4-{(2S)-3-(Allyloxy)-2-[(tert-butoxycarbonyl)amino]-3-oxopropyl}phenoxy)carbonyl]-amino}-2-[(tert-butoxycarbonyl)amino]butanoic acid

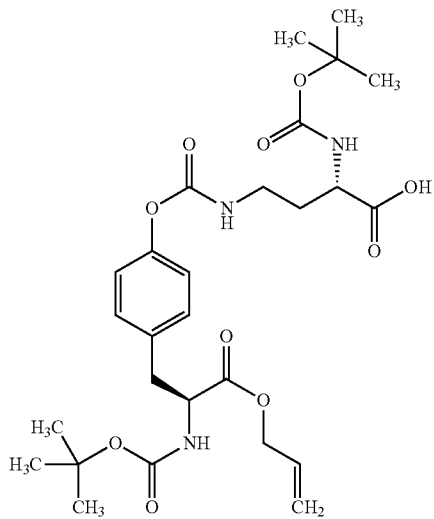 [SMILES: C=CCOC(=O)[C@H](Cc1ccc(OC(=O)NCC[C@H](NC(=O)OC(C)(C)C)C(=O)O)cc1)NC(=O)OC(C)(C)C]

4.0 g (8.22 mmol) of the compound from example 1A was dissolved in 60 ml dichloromethane. 1.795 (8.22 mmol) (2S)-4-Amino-2-[(tert-butoxycarbonyl)amino]butanoic acid and 1.43 ml (8.22 mmol) N,N-diisopropylethylamine were added. The reaction mixture was split into 3 portions. The portions were heated for 30 min in a sealed tube at 75° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 600 ml silica gel. Solvents used were dichloromethane/ethyl acetate 4/1, dichloromethane/ethyl acetate 1/1, dichloromethane/methanol 4/1 and dichloromethane/methanol 1/1. The product-containing fractions were combined and concentrated to dryness under reduced pressure. This gave 4.02 g (6.54 mmol, 80% of theory) of the desired product.

LC-MS (method 1): $R_t$=1.07 min., m/z=564 (M−H)$^−$

Example 3A

Allyl O-({(3S)-4-{[(2R)-1-amino-1-oxo-3-(tritylsulfanyl)propan-2-yl]amino}-3-[(tert-butoxycarbonyl)amino]-4-oxobutyl}carbamoyl)-N-(tert-butoxycarbonyl)-L-tyrosinate

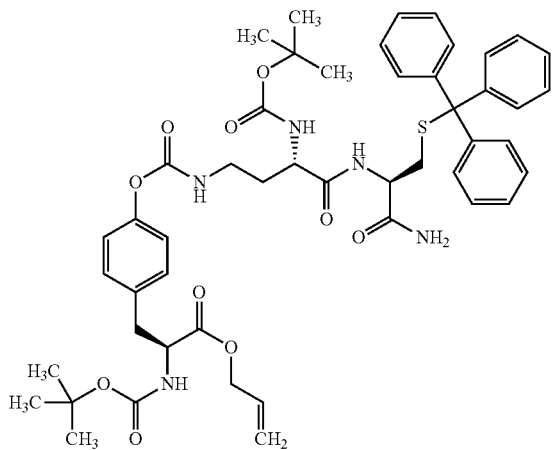 [SMILES: C=CCOC(=O)[C@H](Cc1ccc(OC(=O)NCC[C@H](NC(=O)OC(C)(C)C)C(=O)N[C@@H](CSC(c2ccccc2)(c2ccccc2)c2ccccc2)C(N)=O)cc1)NC(=O)OC(C)(C)C]

2.50 g (4.42 mmol) of the compound from example 2A was dissolved in 100 ml dichloromethane. 1.602 g (4.42 mmol) S-Trityl-L-cysteinamide, 0.77 ml (4.42 mmol) N,N-diisopropylethylamine and 1.68 g (4.42 mmol) HATU were added. The reaction mixture was split into 5 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 600 ml silica gel. Solvents used were dichloromethane/ethyl acetate 2/1, dichloromethane/ethyl acetate 1/1, dichloromethane/methanol 20/1 and dichloromethane/methanol 10/1. The product-containing fractions were combined and concentrated to dryness under reduced pressure. This gave 4.12 g (3.30 mmol, 75% of theory, 73% purity) of the desired product.

LC-MS (method 1): $R_t$=1.36 min., m/z=911 (M+H)$^+$

Example 4A

O-({(3S)-4-{[(2R)-1-Amino-1-oxo-3-(tritylsulfanyl)propan-2-yl]amino}-3-[(tert-butoxycarbonyl)amino]-4-oxobutyl}carbamoyl)-N-(tert-butoxycarbonyl)-L-tyrosine

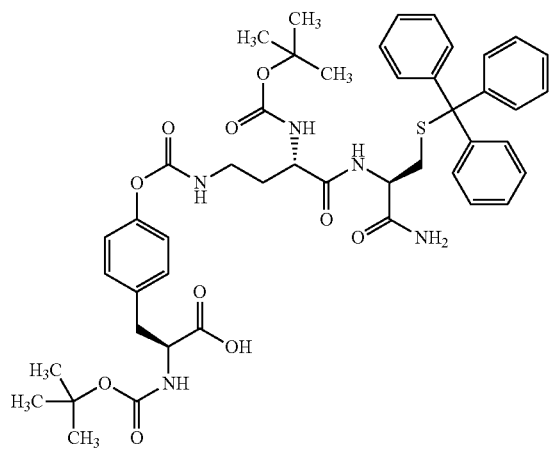 [SMILES: CC(C)(C)OC(=O)N[C@@H](Cc1ccc(OC(=O)NCC[C@H](NC(=O)OC(C)(C)C)C(=O)N[C@@H](CSC(c2ccccc2)(c2ccccc2)c2ccccc2)C(N)=O)cc1)C(=O)O]

4.14 g (4.55 mmol) of the compound from example 3A was dissolved in 90 ml tetrahydrofuran. 3.17 ml (22.8 mmol) triethylamine, 0.86 ml (22.8 mmol) formic acid and 0.526 g (0.455 mmol) tetrakis(triphenylphosphin)palladium(0) were added. The reaction mixture was stirred over night at room temperature. The reaction was diluted with approx. 100 ml water, and twice extracted with approx. 100 ml dichloromethane. The combined organic phases were extracted with brine, dried over sodium sulfate and concentrated to dryness under reduced pressure. The raw product was dissolved in dichloromethane and chromatographed over approx. 500 ml silica gel. Solvents used were dichloromethane, dichloromethane/methanol 20/1 and dichloromethane/methanol 1/1. The product-containing fractions were combined and concentrated to dryness under reduced pressure. This gave 2.62 g raw product of 94.5% purity. The product was further purified by preparative RP-HPLC on a C18 with a water/methanol gradient to yield 2.35 g (2.70 mmol, 59% of theory) pure product.

LC-MS (method 1): $R_t$=1.22 min., m/z=871 (M+H)$^+$ $^1$H-NMR (400 MHz, DMSO-d$_6$, δ/ppm): δ=7.92 (d, 1H), 7.65 (t, 1H), 7.28-7.35 (m, 12H), 7.25-7.28 (t, 3H), 7.15-7.20 (m, 4H), 6.95 (d, 2H), 4.29 (q, 1H), 4.00 (m, 1H), 3.92 (m, 1H), 3.11 (m, 3H), 2.90 (m, 1H), 2.36 (m, 2H), 1.84 (m, 1H), 1.68 (m, 1H), 1.34 (d, 18H).

Example 5A tert-Butyl-methyl(2-oxotetrahydrofuran-3-yl)carbamate

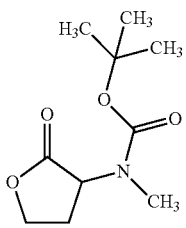

The compound was synthesized according to Alberico, Dino; Paquin, Jean-Francois; Lautens, Mark; Tetrahedron, 2005, vol. 61, p. 6283-6297.

5.18 g (25.7 mmol) tert-Butyl(tetrahydro-2-oxo-3-furanyl)carbamate, 4.81 ml (77.2 mmol) iodomethane were dissolved in 100 ml of dry dimethyl fomamide. The solution was cooled to 0° C. and 1.34 g (60% in mineral oil, 33.5 mmol) sodium hydride was added. The reaction was warmed to room temperature and stirred over night. The reaction mixture was added to approx. 400 ml water and the mixture was extracted three times with approx. 300 ml ethyl acetate. The combined organic phases were dried over sodium sulfate and concentrated to dryness under reduced pressure. This gave 8.70 g (25.7 mmol, 100% of theory, 63% purity) of the desired product.

The analytic data was in accordance with the literature. The product was used in the next synthetic step without further purification.

Example 6A

2-[(tert-Butoxycarbonyl)(methyl)amino]-4-(1,3-di-oxo-1,3-dihydro-2H-isoindol-2-yl)butanoic acid

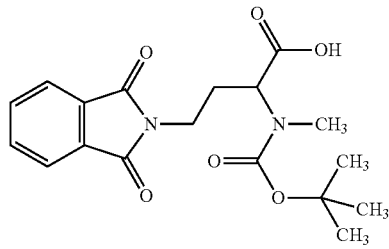 [SMILES: CN(C(=O)OC(C)(C)C)C(CCN1C(=O)c2ccccc2C1=O)C(=O)O]

8.70 g (approx. 25 mmol, approx. 63% purity) of the compound from example 5A was dissolved in 560 ml dimethyl formamide. 8.23 g (44.4 mmol) potassium ophtalimide were added and the reaction mixture was heated to 150° C. for 7 h. Approx. 400 ml of the solvent was removed by rotary evaporation (approx. 60° C., approx. 10 mbar, approx. 30 min.). The reaction mixture was poured onto a mixture of approx. 100 ml water, 200 g ice and 15 ml acetic acid. After melting of the remaining ice the reaction mixture was filtered and the filtrate was extracted 3 times with approx. 100 ml dichloromethane. The combined organic phases were dried over sodium sulfate and concentrated to dryness under reduced pressure. The raw product was dissolved in dichloromethane and chromatographed over approx. 70 ml silica gel. Solvents used were dichloromethane/ethyl acetate 9/1 to dichloromethane/ethyl acetate 6/4. The product-containing fractions were combined and concentrated to dryness under reduced pressure. This gave 2.39 g (6.04 mmol, 24% of theory) product.

LC-MS (method 1): $R_t$=0.92 min, m/z=363 (M+H)$^+$

Example 7A

4-Amino-2-[(tert-butoxycarbonyl)(methyl)amino]butanoic acid

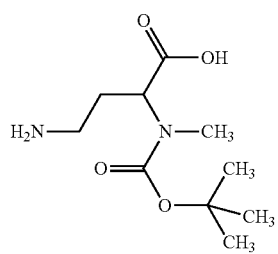 [SMILES: CN(C(=O)OC(C)(C)C)C(CCN)C(=O)O]

11.8 g (32.6 mmol) of the compound from example 6A was dissolved in approx. 640 ml ethanol and 23.8 ml (488 mmol) hydrazine hydrate was added to the reaction mixture. After stirring over night, the reaction mixture was filtered and the filtrate was concentrated to dryness under reduced pressure. The raw product was dissolved in ethanol and approx. 50 g silica gel was added, the solvent was removed under reduced pressure. The resulting solid was added onto a approx. 500 g silica gel column and chromatographed. Solvents used were dichloromethane/methanol 9/1 to dichloromethane/methanol 1/1. The product-containing fractions were combined and concentrated to dryness under reduced pressure. This gave 2.98 g (12.8 mmol, 39% of theory) product.

LC-MS (method 2): $R_t$=0.21 min., m/z=233 (M+H)$^+$
DCI MS (method 5): m/z=233 (M+H)$^+$

Example 8A

4-{[(4-{(2S)-3-(Allyloxy)-2-[(tert-butoxycarbonyl)amino]-3-oxopropyl}phenoxy)carbonyl]-amino}-2-[(tert-butoxycarbonyl)(methyl)amino]butanoic acid

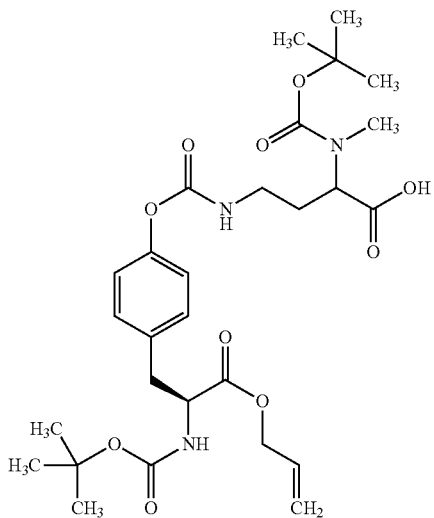 [SMILES: C=CCOC(=O)[C@H](Cc1ccc(OC(=O)NCCC(C(=O)O)N(C)C(=O)OC(C)(C)C)cc1)NC(=O)OC(C)(C)C]

0.931 g (1.92 mmol) of the compound from example 1A was dissolved in 30 ml dichloromethane. 0.455 g (1.92 mmol) of the compound from example 7A was added. The reaction mixture was split into 2 portions. The portions were heated for 30 min in a sealed tube at 80° C. in a microwave synthesizer. From the combined reaction mixture the solvent was removed under reduced pressure. The raw product was purified by preparative RP-HPLC on a C18 column with a water methanol gradient from 9/1 to 1/9. The product-containing fractions were combined and concentrated to dryness under reduced pressure. This gave 0.523 g (0.85 mmol, 44% of theory) of the desired product as a mixture of 2 diastereomers.

LC-MS (method 1): $R_t$=1.08 and 1.11 min., m/z=578 (M–H)$^-$

Example 9A

Allyl O-[(4-{[(2R)-1-amino-1-oxo-3-(tritylsulfanyl)propan-2-yl]amino}-3-[(tert-butoxycarbonyl)-(methyl)amino]-4-oxobutyl)carbamoyl]-N-(tert-butoxycarbonyl)-L-tyrosinate

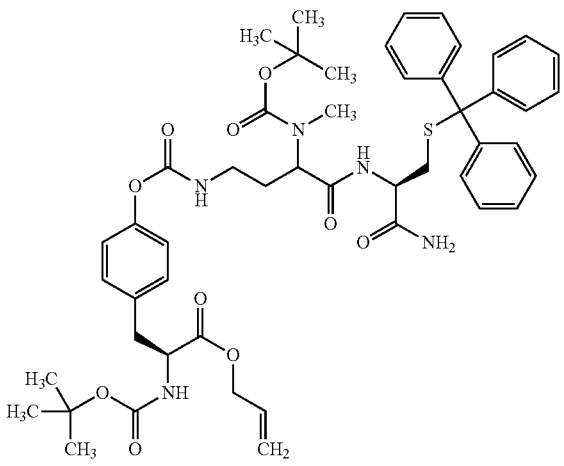 [SMILES: C=CCOC(=O)[C@H](Cc1ccc(OC(=O)NCCC(C(=O)N[C@@H](CSC(c2ccccc2)(c2ccccc2)c2ccccc2)C(N)=O)N(C)C(=O)OC(C)(C)C)cc1)NC(=O)OC(C)(C)C]

2.24 g (3.86 mmol) of the compound from example 8A was dissolved in 100 ml dichloromethane. 1.401 g (3.86 mmol) S-Trityl-L-cysteinamide, 0.67 ml (3.86 mmol) N,N-diisopropylethylamine and 1.47 g (3.86 mmol) HATU were added. The reaction mixture was split into 5 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was purified by preparative RP-HPLC on a C18 column with a water methanol gradient from 9/1 to 1/9. The product-containing fractions were combined and concentrated to dryness under reduced pressure. This gave 3.26 g (2.75 mmol, 71% of theory, 78% purity) of the desired product as a mixture of diastereomers.

LC-MS (method 1): $R_t$=1.41 and 1.43 min., m/z=924 (M+H)$^+$

Example 10A

O-[(4-{[(2R)-1-Amino-1-oxo-3-(tritylsulfanyl)propan-2-yl]amino}-3-[(tert-butoxycarbonyl)-(methyl)amino]-4-oxobutyl)carbamoyl]-N-(tert-butoxycarbonyl)-L-tyrosine

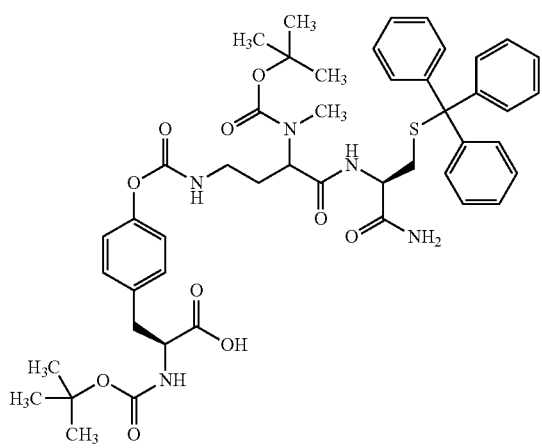 [SMILES: CN(C(=O)OC(C)(C)C)C(CCNC(=O)Oc1ccc(C[C@H](NC(=O)OC(C)(C)C)C(=O)O)cc1)C(=O)N[C@@H](CSC(c1ccccc1)(c1ccccc1)c1ccccc1)C(N)=O]

2.2 g (2.38 mmol) of the compound from example 9A was dissolved in 48 ml tetrahydrofuran. 1.66 ml (11.9 mmol) triethylamine, 0.45 ml (11.9 mmol) formic acid and 0.275 g (0.238 mmol) tetrakis(triphenylphosphin)palladium(0) were added. The reaction mixture was stirred over night at room temperature. The reaction was diluted with approx. 50 ml water and twice extracted with approx. 50 ml dichloromethane. The combined organic phases were extracted with brine, dried over sodium sulfate and concentrated to dryness under reduced pressure. The raw product was dissolved in dichloromethane and chromatographed over approx. 100 g silica gel. Solvents used were dichloromethane, dichloromethane/methanol 50/1 and dichloromethane/methanol 4/1. The product-containing fractions were combined and concentrated to dryness under reduced pressure. This gave 1.44 g (1.61 mmol, 68% of theory) product as a mixture of diastereomers.

LC-MS (method 1): $R_t$=1.20 and 1.24 min., m/z=884 (M+H)$^+$ $^1$H-NMR (400 MHz, DMSO-d$_6$, δ/ppm): δ=8.00 (m, 1H), 7.65-7.90 (m, 4H), 7.18-7.35 (m, 18H), 7.10 (m, 2H), 6.96 (m, 4H), 4.60 (m, 1H), 4.46 (m, 1H), 4.30 (m, 2H), 4.05 (m, 2H), 3.00 (m, 4H), 2.75 (m, 6H), 2.36 (m, 3H), 2.00 (m, 2H), 1.82 (m, 2H), 1.40 (m, 3H), 1.35 (s, 18H).

Example 11A

N$^5$-[(4-{(2S)-3-(Allyloxy)-2-[(tert-butoxycarbonyl)amino]-3-oxopropyl}phenoxy)carbonyl]-N$^2$-(tert-butoxycarbonyl)-L-ornithine

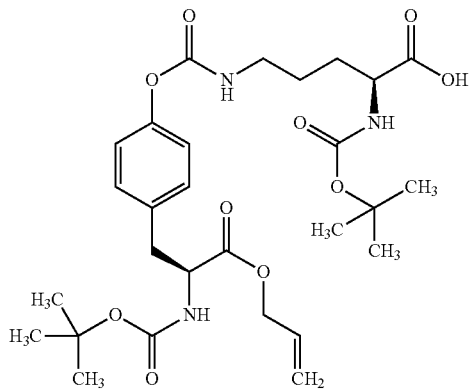 [SMILES: C=CCOC(=O)[C@H](Cc1ccc(OC(=O)NCCC[C@H](NC(=O)OC(C)(C)C)C(=O)O)cc1)NC(=O)OC(C)(C)C]

6.00 g (12.33 mmol) of the compound from example 1A was dissolved in 120 ml dichloromethane. 2.57 g (12.33 mmol) N$^2$-(tert-Butoxycarbonyl)-L-ornithine was added. The reaction mixture was split into 6 portions. The portions were heated for 90 min in a sealed tube at 75° C. in a microwave synthesizer. The combined reaction mixture was extracted with approx. 100 ml saturated ammonium chloride solution. The aqueous phase was twice back extracted with approx. 30 ml dichloromethane each. The combined organic phases were extracted with approx. 50 ml brine and dried over sodium sulfate. The solvent was removed under reduced pressure. The raw product was dissolved in dichloromethane and chromatographed over approx. 600 ml silica gel. Solvents used were dichloromethane, dichloromethane/methanol 40/1 to dichloromethane/methanol 1/1. The product-containing fractions were combined and concentrated to dryness under reduced pressure. This gave 2.63 g (4.06 mmol, 33% of theory, 89% purity) of the desired product.

LC-MS (method 1): $R_t$=1.03 min., m/z=578 (M−H)$^-$

Example 12A

N$^5$-[(4-{(2S)-3-(Allyloxy)-2-[(tert-butoxycarbonyl)amino]-3-oxopropyl}phenoxy)carbonyl]-N$^2$-(tert-butoxycarbonyl)-L-ornithyl-5-trityl-L-cysteinamide

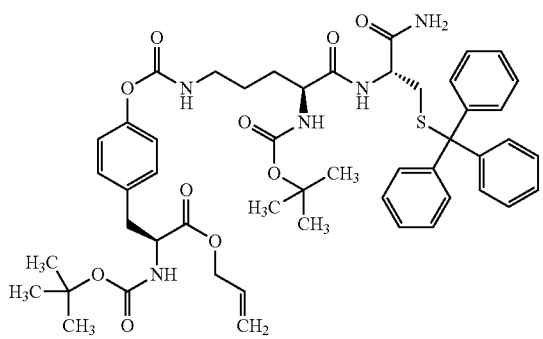 [SMILES: C=CCOC(=O)[C@H](Cc1ccc(OC(=O)NCCC[C@H](NC(=O)OC(C)(C)C)C(=O)N[C@@H](CSC(c2ccccc2)(c2ccccc2)c2ccccc2)C(N)=O)cc1)NC(=O)OC(C)(C)C]

1.20 g (2.07 mmol) of the compound from example 11A was dissolved in 48 ml dichloromethane. 0.750 g (2.07 mmol) S-Trityl-L-cysteinamide, 0.36 ml (2.07 mmol) N,N-diisopropylethylamine and 0.787 g (2.07 mmol) HATU were added. The reaction mixture was split into 3 portions. The portions were heated for 30 min in a sealed tube at 60° C. in a microwave synthesizer. From the combined reaction mixture the solvent was removed by rotary evaporation (approx. 40° C., approx. 200 mbar, approx. 30 min.). The raw product was dissolved in dichloromethane and chromatographed over approx. 400 ml silica gel. Solvents used were dichloromethane/ethyl acetate 2/1, dichloromethane/ethyl acetate 1/1. The product-containing fractions were combined and concentrated to dryness under reduced pressure. This gave 1.30 g (1.5 mmol, 56% of theory, 82% purity) of the desired product.

LC-MS (method 1): $R_t$=1.35 min, m/z=924 (M+H)$^+$

Example 13A $N^2$-(tert-Butoxycarbonyl)-$N^5$-[(4-{(2S)-2-[(tert-butoxycarbonyl)amino]-2-carboxyethyl}phenoxy)-carbonyl]-L-ornithyl-5-trityl-L-cysteinamide

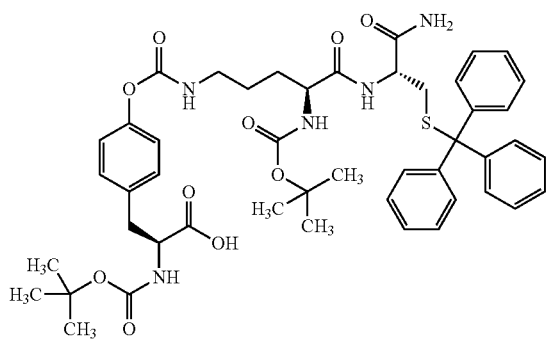 [SMILES: CC(C)(C)OC(=O)N[C@@H](Cc1ccc(OC(=O)NCCC[C@H](NC(=O)OC(C)(C)C)C(=O)N[C@@H](CSC(c2ccccc2)(c2ccccc2)c2ccccc2)C(N)=O)cc1)C(=O)O]

3.06 g (2.33 mmol) of the compound from example 12A was dissolved in 46 ml tetrahydrofuran. 1.63 ml (11.6 mmol) triethylamine, 0.44 ml (11.6 mmol) formic acid and 0.265 g (0.233 mmol) tetrakis(triphenylphosphin)palladium(0) were added. The reaction mixture was stirred over night at room temperature. The reaction was diluted with approx. 50 ml water and twice extracted with approx. 50 ml dichloromethane. The combined organic phases were extracted with brine, dried over sodium sulfate and concentrated to dryness under reduced pressure. The raw product was dissolved in dichloromethane and chromatographed over approx. 500 ml silica gel. Solvents used were dichloromethane, dichloromethane/methanol 40/1 and dichloromethane/methanol 1/1. The product-containing fractions were combined and concentrated to dryness under reduced pressure. This gave 1.40 g raw product of 86% purity. The product was further purified by preparative RP-HPLC on a C18 column with a water/methanol gradient to yield 2 fractions: 0.93 g product (45% of theory).

LC-MS (method 1): $R_t$=1.18 min., m/z=885 (M+H)$^+$ $^1$H-NMR (400 MHz, DMSO-$d_6$, δ/ppm): δ=7.89 (d, 1H), 7.65 (t, 1H), 7.25-7.35 (m, 12H), 7.20-7.25 (m, 6H), 7.10-7.20 (m, 3H), 6.95 (d, 2H), 4.29 (m, 1H), 4.05 (m, 1H), 3.88 (m, 1H), 3.11 (d, 1H), 3.00 (m, 4H), 2.75 (m, 2H), 2.36 (m, 3H), 1.64 (m, 1H), 1.51 (m, 3H), 1.36 (s, 9H), 1.32 (s, 9H).

Example 14A

Tentagel Based Amide Resin Bound ADM (2-52)

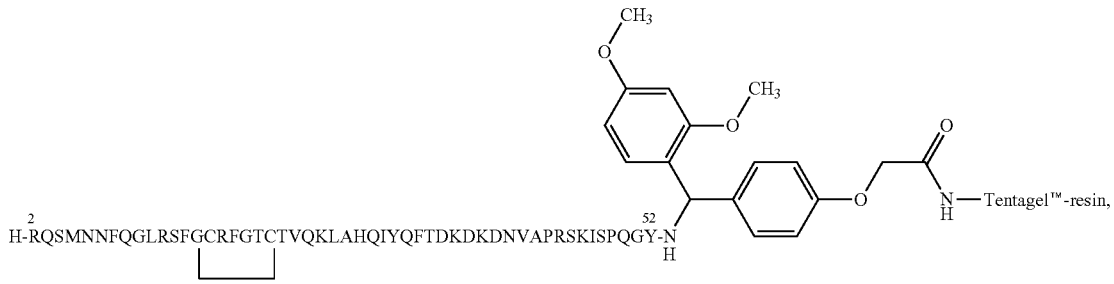

The peptide was assembled stepwise on a Tentagel based amide resin on an automated peptide synthesizer (Protein Technologies Inc. Symphony). 8 poly-propylene reaction vessels were used in parallel performing the identical chemistry. Each vessel was loaded with 0.05 mmol Tentagel based Rink resin for a total batch size of 0.4 mmol.

Each amino acid is added in 8 fold molar access with regard to the loading of the resin. The amino acids were Fmoc protected as the N-terminal protecting group and the protecting groups indicated below were used for side chain functionalities. Also 188 mg (0.59 mmol, 7.8 eq.) TBTU and 0.21 ml (1.2 mmol, 16 eq.) DIEA were added. Reactions were performed in DMF as solvent, whereas DMF was used in an amount sufficient to swell the resin and agitate it freely. Reaction time per amino acid was approx. 1 hour. Cleavage of the Fmoc protecting groups was achieved using 20% piperidine/DMF, whereas 20% piperidine/DMF was used in an amount sufficient to swell the resin and agitate it freely.

The coupling sequence was as follows:
1. Tyr(tBu) (Tyr=Y=AA 52 of human ADM)
2. Gly (Gly=G=AA 51 of human ADM)
3. Gln(Trt) (Gln=Q=AA 50 of human ADM)
4. Pro (Pro=P=AA 49 of human ADM)
5. Ser(tBu) (Ser=S=AA 48 of human ADM)
6. Ile (Ile=I=AA 47 of human ADM)
7. Lys(Boc) (Lys=K=AA 46 of human ADM)
8. Ser(tBu) (Ser=S=AA 45 of human ADM)
9. Arg(pbf) (Arg=R=AA 44 of human ADM)
10. Pro (Pro=P=AA 43 of human ADM)
11. Ala (Ala=A=AA 42 of human ADM)
12. Val (Val=V=AA 41 of human ADM)
13. Asn(Trt) (Asn=N=AA 40 of human ADM)
14. Asp(OtBu) (Asp=D=AA 39 of human ADM)
15. Lys(Boc) (Lys=K=AA 38 of human ADM)
16. Asp(OtBu) (Asp=D=AA 37 of human ADM)
17. Lys(Boc) (Lys=K=AA 36 of human ADM)
18. Asp(OtBu) (Asp=D=AA 35 of human ADM)
19. Thr(tBu) (Thr=T=AA 34 of human ADM)
20. Phe (Phe=F=AA 33 of human ADM)
21. Gln(Trt) (Gln=Q=AA 32 of human ADM)
22. Tyr(tBu) (Tyr=Y=AA 31 of human ADM)
23. Ile (Ile=I=AA 30 of human ADM)
24. Gln(Trt) (Gln=Q=AA 29 of human ADM)
25. His(Trt) (His=H=AA 28 of human ADM)
26. Ala (Ala=A=AA 27 of human ADM)
27. Leu (Leu=L=AA 26 of human ADM)
28. Lys(Boc) (Lys=K=AA 25 of human ADM)
29. Gln(Trt) (Gln=Q=AA 24 of human ADM)
30. Val (Val=V=AA 23 of human ADM)
31. Thr(tBu) (Thr=T=AA 22 of human ADM)
32. Cys(Trt) (Cys=C=AA 21 of human ADM)
33. Thr(tBu) (Thr=T=AA 20 of human ADM)
34. Gly (Gly=G=AA 19 of human ADM)
35. Phe (Phe=F=AA 18 of human ADM)
36. Arg(pbf) (Arg=R=AA 17 of human ADM)
37. Cys(Acm) (Cys=C=AA 16 of human ADM)
38. Gly (Gly=G=AA 15 of human ADM)
39. Phe (Phe=F=AA 14 of human ADM)
40. Ser(tBu) (Ser=S=AA 13 of human ADM)
41. Arg(pbf) (Arg=R=AA 12 of human ADM)
42. Leu (Leu=L=AA 11 of human ADM)
43. Gly (Gly=G=AA 10 of human ADM)
44. Gln(Trt) (Gln=Q=AA 9 of human ADM)
45. Phe (Phe=F=AA 8 of human ADM)
46. Asn(Trt) (Asn=N=AA 7 of human ADM)
47. Asn(Trt) (Asn=N=AA 6 of human ADM)
48. Met (Met=M=AA 5 of human ADM)
49. Ser(tBu) (Ser=S=AA 4 of human ADM)
50. Gln(Trt) (Gln=Q=AA 3 of human ADM)
51. Arg(pbf) (Arg=R=AA 2 of human ADM)

On-resin oxidation was achieved using Cys(Trt) and Cys(Acm) protection with concomitant cleavage of protecting groups and oxidation to a disulfide bond using Iodine (8 equivalents of Iodine plus 8 equivalents of DIEA with a reaction time of 30 minutes). Oxidation was confirmed by sample cleavage and analysis using HPLC and MALDI-MS. The 8 batches were pooled for further use.

Example 15A

O-{[(3S)-3-Amino-4-{[(2R)-1-amino-1-oxo-3-sulfanylpropan-2-yl]amino}-4-oxobutyl]-carbamoyl}-L-tyrosyl-adrenomedullin (2-52)

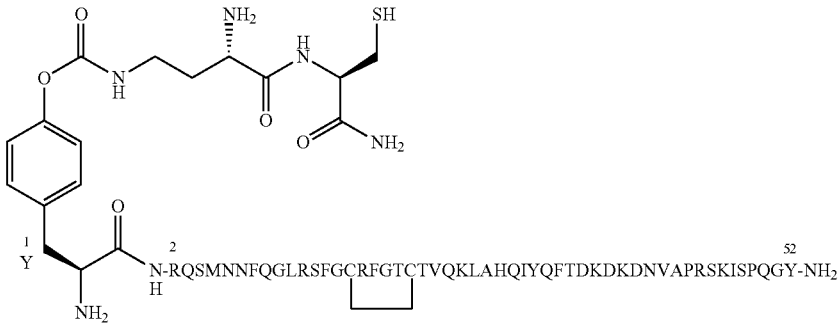

To 0.075 mmol of the compound of example 14A 520 mg (0.6 mmol, 8 eq.) of the compound of example 4A were added. Also 188 mg (0.59 mmol, 7.8 eq.) TBTU and 0.21 ml (1.2 mmol, 16 eq.) DIEA were added. The reaction was performed with DMF as solvent, whereas DMF was used in an amount sufficient to swell the resin and agitate it freely. Reaction time was approx. 1 hour at room temperature. The peptide was cleaved from the resin with concomitant global deprotection using concentrated TFA in an amount sufficient to swell the resin and agitate it freely, whereas TFA contains scavengers (1-5% each of water, phenol, thioanisole and 1,2-ethanediol), with a reaction time of 2½ hrs. The crude product was lyophilised and purified by RP-chromatography using 0.1% TFA in water and 0.1% TFA in acetonitrile as mobile phases to ensure that the pH remains below 4 at all times during the purification and lyophilisation process. All fractions containing the correct ion by MALDI-MS analysis were pooled. The yield was 44.0 mg of partially purified peptide (approx. 0.0035 mmol, approx. 4.7% of theory; estimated purity: approx. 50%, main impurity: ADM (2-52)).

MALDI MS (method 6): m/z=6275 (M+H)$^+$ and 5866 (impurity: (ADM (2-52)+H)$^+$)

Example 16A

O-{[4-{[(2R)-1-Amino-1-oxo-3-sulfanylpropan-2-yl]amino}-3-(methylamino)-4-oxobutyl]-carbamoyl}-L-tyrosyl-adrenomedullin (2-52)

To 0.075 mmol of the compound of example 14A 530 mg (0.6 mmol, 8 eq.) of the compound of example 10A were added. Also 188 mg (0.59 mmol, 7.8 eq.) TBTU and 0.21 ml (1.2 mmol, 16 eq.) DIEA were added. The reaction was performed with DMF as solvent, whereas DMF was used in an amount sufficient to swell the resin and agitate it freely. Reaction time was approx. 1 hour at room temperature. The peptide was cleaved from the resin with concomitant global deprotection using concentrated TFA in an amount sufficient to swell the resin and agitate it freely, whereas TFA contains scavengers (1-5% each of water, phenol, thioanisole and 1,2-ethanediol), with a reaction time of 2½ hrs. The crude product was lyophilised and purified by RP-chromatography using 0.1% TFA in water and 0.1% TFA in acetonitrile as mobile phases to ensure that the pH remains below 4 at all times during the purification and lyophilisation process. All fractions containing the correct ion by MALDI-MS analysis were pooled. The yield was 34.0 mg of partially purified peptide (approx. 0.0026 mmol, approx. 3.5% of theory; estimated purity: approx. 50%, main impurity: ADM (2-52)).

MALDI MS (method 6): m/z=6289 (M+H)$^+$ and 5866 (impurity: (ADM (2-52)+H)$^+$)

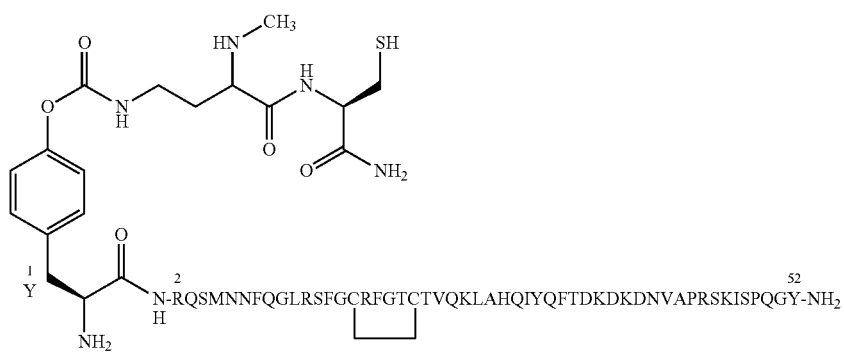

Example 17A

O-{[(4R)-4-Amino-5-{[(2R)-1-amino-1-oxo-3-sulfanylpropan-2-yl]amino}-5-oxopentyl]-carbamoyl}-L-tyrosyl-adrenomedullin (2-52)

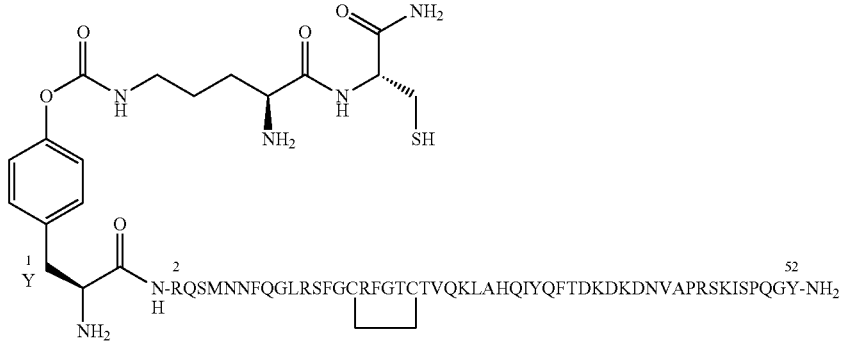

To 0.075 mmol of the compound of example 14A 530 mg (0.6 mmol, 8 eq.) of the compound of example 13A were added. Also 188 mg (0.59 mmol, 7.8 eq.) TBTU and 0.21 ml (1.2 mmol, 16 eq.) DIEA were added. The reaction was performed with DMF as solvent, whereas DMF was used in an amount sufficient to swell the resin and agitate it freely. Reaction time was approx. 1 hour at room temperature. The peptide was cleaved from the resin with concomitant global deprotection using concentrated TFA in an amount sufficient to swell the resin and agitate it freely, whereas TFA contains scavengers (1-5% each of water, phenol, thioanisole and 1,2-ethanediol), with a reaction time of 2½ hrs. The crude product was lyophilised and purified by RP-chromatography using 0.1% TFA in water and 0.1% TFA in acetonitrile as mobile phases to ensure that the pH remains below 4 at all times during the purification and lyophilisation process. All fractions containing the correct ion by MALDI-MS analysis were pooled. The yield was 47 mg of partially purified peptide (approx. 0.0037 mmol, approx. 5.0% of theory; estimated purity: approx. 50%, main impurity: ADM (2-52)).

MALDI MS (method 6): m/z=6289 (M+H)$^+$ and 5866 (impurity: (ADM (2-52)+H)$^+$)

Working Examples

Example 1

O-{[(3S)-3-Amino-4-({(2R)-1-amino-3-[(2,5-dioxo-1-{3-oxo-3-[(2-{ω-methoxy-polyoxyethylen[40 kDa]}ethyl)amino]propyl}pyrrolidin-3-yl)sulfanyl]-1-oxopropan-2-yl}amino)-4-oxobutyl]carbamoyl}-L-tyrosyl-adrenomedullin (2-52)

44 mg of the crude peptide of example 15A were stirred with 426 mg (10.5 mmol, 1.5 eq, sourced from Dr. Reddys) 40 kDa methoxy poly(ethylene glycol) maleimido propionamide in 9 ml citrate buffer of pH 4 over night at room temperature. The crude reaction mixture was injected in two portions onto a preparative HPLC system with a Phenomenex Luna 10μ Proteo C5 100A AXIA 250 mm×21.2 mm column and chromatographed with a water/acetonitrile (both with 0.1% TFA) gradient. The fractions were collected in test tubes of 20 ml on an automated fraction collector. To ensure sufficient acidity each vial was filled with 0.5 ml acetic acid prior to collection.

ADM (2-52), which is the side product of example 15A and which did not undergo PEGylation in this reaction, as well as unreacted PEG were removed completely.

All fractions containing example 1 were combined. Acetonitrile was partially removed on a rotary evaporator at 30° C. water bath temperature and approx. 50 mbar for approx. 30 min After addition of 0.5 ml acetic acid, the remaining solution was lyophilized. The total yield of example 1 was 109 mg (2.35 mmol, 33% of theory).

HPLC (method 3): R$_t$=4.23-4.30 min

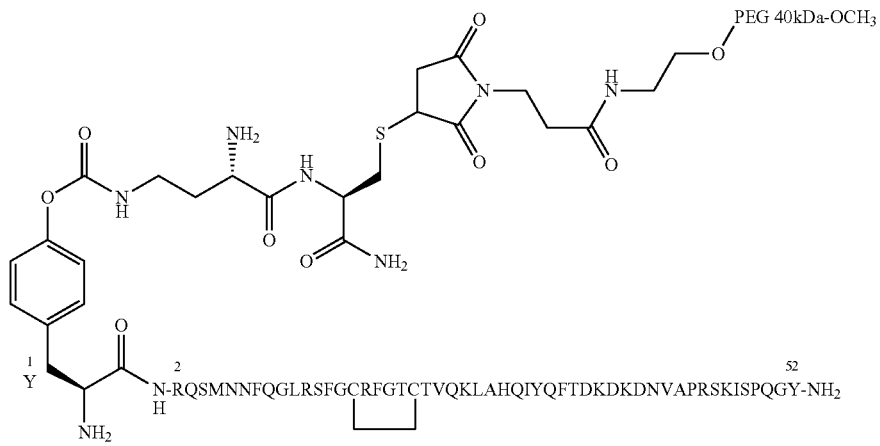

Example 2

O-{[3-N-Methyl-amino-4-({(2R)-1-amino-3-[(2,5-dioxo-1-{3-oxo-3-[(2-{ω-methoxy-polyoxyethylen[40 kDa]}ethyl)amino]propyl}pyrrolidin-3-yl)sulfanyl]-1-oxopropan-2-yl}amino)-4-oxobutyl]carbamoyl}-L-tyrosyl-adrenomedullin (2-52)

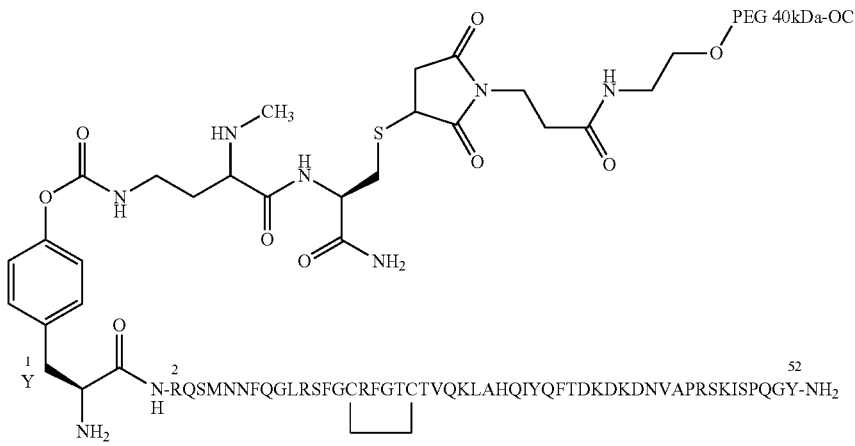

15 mg of the crude peptide of example 16A were stirred with 145 mg (3.58 μmol, 1.5 eq, sourced from Dr. Reddys) 40 kDa methoxy poly(ethylene glycol) maleimido propionamide in 5 ml citrate buffer of pH 4 over night at room temperature. The crude reaction mixture was injected onto a preparative HPLC system with a Phenomenex Jupiter 10μ C18 300A 250 mm×21.2 mm column and chromatographed with a water/acetonitrile (both with 0.1% TFA) gradient. The fractions were collected in test tubes of 20 ml on an automated fraction collector. To ensure sufficient acidity each vial was filled with 0.5 ml acetic acid prior to collection.

ADM (2-52), which is the side product of example 16A and which did not undergo PEGylation in this reaction, as well as unreacted PEG were removed completely.

All fractions containing example 2 were combined. Acetonitrile was partially removed on a rotary evaporator at 30° C. water bath temperature and approx. 50 mbar for approx. 30 min.

After addition of 0.5 ml acetic acid, the remaining solution was lyophilized. The total yield of example 2 was 50 mg (1.08 μmol, 43% of theory).

HPLC (method 4): $R_t$=2.02-2.08 min

Example 3

O-{[(4S)-4-Amino-5-({(2R)-1-amino-3-[(2,5-dioxo-1-{3-oxo-3-[(2-{ω-methoxy-polyoxyethylen[40 kDa]}ethyl)amino]propyl}pyrrolidin-3-yl)sulfanyl]-1-oxopropan-2-yl}amino)-5-oxopentyl]carbamoyl}-L-tyrosyl-adrenomedullin (2-52)

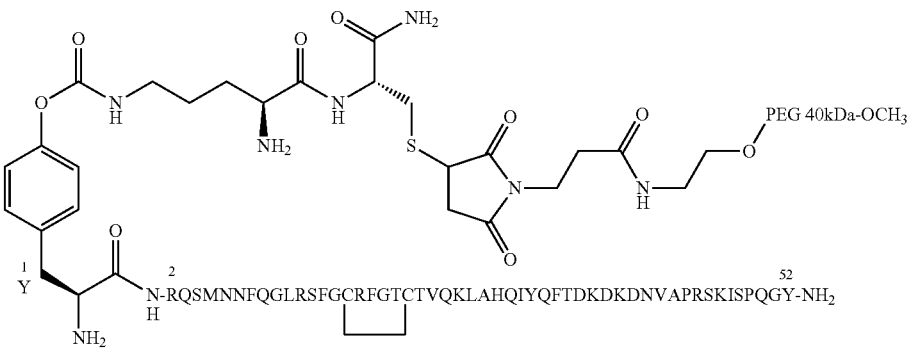

15 mg of the crude peptide of example 17A were stirred with 145 mg (3.58 μmol, 1.5 eq, sourced from Dr. Reddys) 40 kDa methoxy poly(ethylene glycol) maleimido propionamide in 5 ml citrate buffer of pH 4 over night at room temperature. The crude reaction mixture was injected onto a preparative HPLC system with a Phenomenex Jupiter 10μ Proteo 90A AXIA 250 mm×21.2 mm column and chromatographed with a water/acetonitrile (both with 0.1% IFA) gradient. The fractions were collected in test tubes of 20 ml on an automated fraction collector. To ensure sufficient acidity each vial was filled with 0.5 ml acetic acid prior to collection.

ADM (2-52), which is the side product of example 17A and which did not undergo PEGylation in this reaction, as well as unreacted PEG were removed completely.

All fractions containing example 3 were combined. Acetonitrile was partially removed on a rotary evaporator at 30° C. water bath temperature and approx. 50 mbar for approx. 30 min.

After addition of 0.5 ml acetic acid, the remaining solution was lyophilized. The total yield of example 3 was 19.5 mg (0.42 µmol, 17% of theory).

HPLC (method 4): $R_t$=2.02-2.08 min

B. ASSESSMENT OF PHARMACOLOGICAL ACTIVITY

The suitability of the compounds according to the invention for treatment of diseases can be demonstrated using the following assay systems:

1) Test Descriptions (In Vitro)

1a) Tests on a Recombinant Adrenomedullin-Receptor Reporter Cell

The activity of the compounds according to the invention is quantified with the aid of a recombinant Chinese hamster ovary (CHO) cell line that carries the human adrenomedullin-receptor. Activation of the receptor by ligands can be measured by aequorin luminescence. Construction of the cell line and measurement procedure has been described in detail [Wunder F., Rebmann A., Geerts A, and Kalthof B., *Mol Pharmacol*, 73, 1235-1243 (2008)]. In brief: Cells are seeded on opaque 384-well microtiter plates at a density of 4000 cells/well and are grown for 24 h. After removal of culture medium, cells are loaded for 3 h with 0.6 µg/ml coelenterazine in $Ca^{2+}$-free Tyrode solution (130 mM sodium chloride, 5 mM potassium chloride, 20 mM HEPES (4-(2-hydroxyethyl)-1-piperazineethanesulfonic acid), 1 mM magnesium chloride, and 4.8 mM sodium hydrogen carbonate, pH 7.4) supplemented with 0.2 mM 3-Isobutyl-1-methylxanthine (IBMX) in a cell culture incubator. Compounds are added for 6 min in calcium$^{2+}$-free Tyrode solution containing 0.1% bovine serum albumin. Immediately before adding calcium$^{2+}$ to a final concentration of 3 mM measurement of the aequorin luminescence is started by use of a suitable luminometer. Luminescence is measured for 60 s. In a typical experiment compounds are tested in a concentration range of $1\times10^{-13}$ to $3\times10^{-6}$ M.

In order to determine the release of active adrenomedullin from compounds according to the invention, compounds are incubated at different concentrations for different time spans up to 24 h in Tyrode solution supplemented with fetal calf serum, cell culture medium or plasma from different species at pH 7.4. Calcium$^{2+}$ content of the respective incubation media is buffered by addition of 4 mM EDTA (ethylene diamine tetraacetic acid) before adding samples to the adrenomedullin-receptor reporter cell.

After appropriate preincubation, the embodiment examples activate the adrenomedullin-receptor reporter cell more potently than before preincubation. This is indicated by the fact that $EC_{50}$ values are determined by a factor of up to 10 smaller after preincubation than before and is explainable by the release of active adrenomedullin from the compounds.

Representative $EC_{50}$ values for the embodiment examples before and after incubation for 24 h in buffer supplemented with 2.5% fetal calf serum are given in the following Table 1:

TABLE 1

| Example no. | $EC_{50}$ T = 0 h [nM] | $EC_{50}$ T = 24 h [nM] |
| --- | --- | --- |
| ADM | 0.5 | 2.5 |
| 1 | 110 | 8.4 |
| 2 | >1000 | 161 |
| 3 | 124 | 12.3 |

1b) Transcellular Electrical Resistance Assays in Endothelial Cells

The activity of the compounds according to the invention is characterized in in vitro-permeability assays in human umbilical venous cells (HUVEC, Lonza). By use of the ECIS apparatus (ECIS: Electric Cell-substrate Impedance Sensing; Applied Biophysics Inc; Troy, N.Y.) changes of transendothelial electrical resistance (TEER) over an endothelial monolayer are continuously measured by use of a small gold electrode on which the cells have been seeded. HUVEC are grown on the 96-well sensor electrode plates (96W1E, Ibidi GmbH, Martinsried) to confluent monolayers and hyperpermeability can be induced by inflammatory stimuli such as Thrombin, TNF-α, IL-1β, VEGF, Histamine and hydrogen peroxide which all have been demonstrated to cause break down of endothelial cell contacts and reduction of TEER. Thrombin is used at a final concentration of 0.5 U/ml. Test compounds are added before or after addition of thrombin. In a typical experiment compounds are tested in a concentration range of $1\times10^{-10}$ to $1\times10^{-6}$ M.

The embodiment examples inhibit the thrombin induced hyperpermeability in this test at concentrations of ≤$10^{-6}$ M.

1c) In Vitro-Permeability Assays in Endothelial Cells

In another in vitro model of endothelial hyperpermeability the activity of compounds according to the invention is examined with respect to modulation of macromolecular permeability. Human umbilical vein endothelial cells (HUVECS) are grown to confluency on fibronectin-coated Transwell® filter membranes (24-well plates, 6.5 mm-inserts with 0.4 µM polycarbonate membrane; Costar #3413) which separate an upper from a lower tissue culture chamber with endothelial cells growing on the bottom of the upper chamber. The medium of the upper chamber is supplemented with 250 µg/ml of 40 kDa FITC-Dextran (Invitrogen, D1844). Hyperpermeability of the monolayer is induced by addition of thrombin to a final concentration of 0.5 U/ml. Medium samples are collected from the lower chamber every 30 min and relative fluorescence as a parameter for changes of macromolecular permeability over time is measured in a suitable fluorimeter. Thrombin challenge induces almost a doubling of FITC-dextran transition across the endothelial monolayers. In a typical experiment compounds are tested in a concentration range of $1\times10^{-10}$ to $1\times10^{-6}$ M.

The embodiment examples inhibit the thrombin induced hyperpermeability in this test at concentrations of ≤$10^{-6}$ M.

2. Test Descriptions (In Vivo)

2a) Measurement of Blood Pressure and Heart Rate in Telemetered, Normotensive Wistar Rats The cardiovascular effects induced by compounds according to the invention are investigated in freely moving conscious female Wistar rats (body weight>200 g) by radio-telemetric measurement of blood pressure and heart rate. Briefly, the telemetric system (DSI Data Science International, MN, USA) is composed on 3 basic elements: implantable transmitters (TA11PA-C40), receivers (RA1010) and a computer-based acquisition software (Dataquest™ A.R.T. 4.1 for Windows). Rats are instrumented with pressure implants for chronic use at least 14 days prior to the experiments. The sensor catheter is tied with 4-0 suture several times to produce a stopper 0.5 cm from the tip of the catheter. During catheter implantation rats are anesthetized with pentobabital (Nembutal, Sanofi: 50 mg/kg i.p.). After shaving the abdominal skin, a midline abdominal incision is made, and the fluid-filled sensor catheter is inserted upstream into the exposed descending aorta between the iliac bifurcation and the renal arteries. The catheter is tied several times at the stopper. The tip of the telemetric catheter is located just caudal to the renal arteries and secured by tissue adhesive. The transmitter body is affixed to the inner peritoneal wall before closure of abdomen. A two-layer closure of the abdominal incision is used, with individual suturing of the peritoneum and the muscle wall followed by closure of the outer skin. For postsurgical protection against infections and pain a single dosage of an antibiotic (Oxytetracyclin 10% R, 5.0 ml/bo s.c., beta-pharma GmbH&Co, Germany) and analgesic is injected (Rimadyl R, 5.0 ml/kg s.c., Pfizer, Germany). The hardware configuration is equipped for 24 animals. Each rat cage is positioned on top of an individual receiver platform. After activation of the implanted transmitters, an on-line data acquisition system, samples data and converts telemetric pressure signals to mm Hg. A barometric pressure reference allows for relation of absolute pressure (relative to vacuum) to ambient atmospheric pressure. Data acquisition software is predefined to sample hemodynamic data for 10-s intervals every 5 minutes. Data collection to file is started 2 hours before administration of test compounds and finished after completion of 24-h cycles. In a typical experiment test compounds are administered as bolus either subcutaneously or intravenously at does of 1 to 1000 µg/kg body weight (as referred to the peptide component).

Wild type adrenomedullin (Bachem, H-2932) induces blood pressure reduction in this test with duration of ≤4 h when tested at doses of ≤300 µg/kg body weight [FIG. 1].

FIG. 1: 24 hour profiles of mean arterial blood pressure (MABP) recorded from telemeterd normotensive female Wistar rats after subcutaneous administration of ADM or vehicle as indicated (dotted line). Data points were plotted as means±SEM of averaged 30 min intervals from 4 animals per group. One hour after administration animals treated with ADM showed a mean reduction of MABP of almost 20% at peak (filled circles). After about 3.5 hours MABP had returned to base line levels and was in the range of that of vehicle treated animals (open circles).

Figure 2:
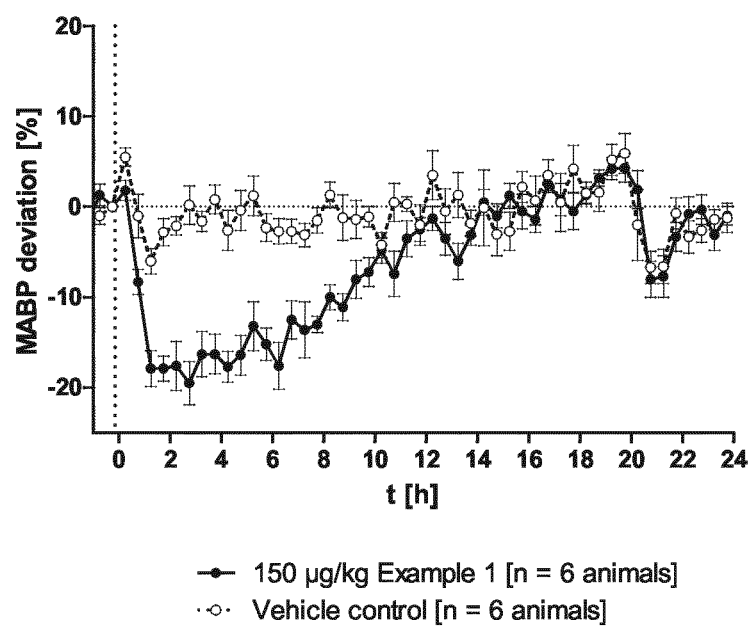

In this test substances according to the present invention induce blood pressure reduction of up to 10 h at doses of ≤500 µg/kg body weight (as referred to the peptide component) [FIG. 2].

FIG. 2: 24 hour profiles of mean arterial blood pressure (MABP) recorded from telemeterd normotensive female Wistar rats after subcutaneous administration of example 1 or vehicle as indicated (dotted line). Data points were plotted as means±SEM of averaged 30 min intervals from 6 animals per group. Administration of example 1 at a dose of 150 µg/kg (as referred to the peptide component) reduced MABP by about 15 to 19% until 6 h after administration (filled circles). Between 6 h and 14 h after administration MABP gradually returned to baseline values and finally was in the range of that of vehicle treated animals.

2b) Skin Vascular Leak Assay in Wistar Rats

An intracutaneous histamine challenge test is employed to assess the effect of compounds according to the invention on vascular barrier function in healthy animals. Male Sprague Dawley rats (body weight>200 g) are anesthetized with isoflurane (2%-3% in ambient air) and brought into supine position. The abdomen is shaved and a catheter is inserted into the femoral vein. Vehicle only (0.5 ml PBS+0.1% bovine serum albumin) or test compounds at appropriate doses are administered as i.v. bolus injections. After 15 min a second injection of 100 µl/kg 2% Evans blue (Sigma) solution is administered and immediately thereafter 100 µl of histamine solutions of appropriate concentrations (for example 0-2.5-5-10-20-40 µg/ml) are injected intracutaneously into the abdominal skin. Evans blue is a highly plasma protein bound dye and therefore used as an indicator for protein-rich fluid extravasation and vascular leakage. 30 min after this procedure the rats are sacrificed by an overdose of isoflurane and subsequent neck dislocation and the abdominal skin is excised. The wheals are excised by use of an 8 mm biopsy punch, the tissue samples are weighted and transferred to formamide for 48 h in order to extract the Evans blue. Samples are measured at 620 nM and 750 nM wavelength on a suitable photometer and Evans blue content of the samples is corrected for heme pigments according to the formula A620 (corrected)=A620−(1.426×A750+0.030) and calculated against a standard curve. [method adapted from Wang L. F., Patel M., Razavi H. M., Weicker S., Joseph M. G., McCormack D. G., Mehta S., *Am. Respir Crit Care Med,* 165(12), 1634-9 (2002)].

Substances according to the present invention reduce extravasation of protein rich plasma fluid induced by histamine challenge in this test.

2c) Intra-Tracheal Instillation of LPS in Mice

An intra-tracheal challenge with lipopolysaccharide (LPS) is employed to examine the effects of compounds according to the invention on acute lung injury. Male BALB/c mice (average animal weight 20-23 g) are anesthetized with isoflurane (7%) and LPS from *E. coli* (e.g. serotype 055:B5; Sigma) is instilled in 100 µl saline by use of a micropipette. Typical doses of LPS used for challenge are in the range of 1 to 10 mg/kg body weight. At different time points before and after instillation test compounds are administered by the subcutaneous route. Typical doses are in the range of 1 to 300 µg/kg body weight. In this test typical time points of administration of test compounds are 15 min before or 1 h after LPS challenge. 48 hours after instillation of LPS mice are deeply anesthetized with isoflurane and sacrificed by dislocation of the neck. After cannulation of the trachea lavage of the bronchoalveolar space with 0.5 ml ice-cold saline is performed. Lungs are prepared and weighted. Cells in the bronchoalveolar lavage fluid (BALF) are counted on a cell counter (Cell Dyn 3700, Abbott). In this test lung weight as a measure for lung edema is reproducibly found to be increased by about 50% or more over sham controls 48 hours after LPS challenge. As lung weights show only very low variability in the groups, the absolute lung weight is used as parameter. The counts for white blood cells are always found to be significantly increased over control in the BALF after LPS challenge.

Administration of substances according to the present invention resulted in significantly reduced lung weight and white blood cell counts in the BALF after 48 h when administered as bolus at doses≤300 µg/kg body weight (as referred to the peptide component).

2d) Induction of Acute Lung Injury in Mini Pigs

Acute lung injury is induced in anesthetized mini pigs by use of lipopolysaccharide (LPS) or oleic acid as challenges. In detail: female Göttingen minipigs of ca. 3.5 to 5.5 kg body weight (Ellegaard, Denmark) are kept anesthetized by an continuous i.v.-infusion of Ketavet®, Dormicum® and Pancuronium® after premedication with an intramuscular injection of Ketavet®/Stresnil®. After intratracheal intubation animals are artificially ventilated using a pediatric respirator (Sulla 808V; Dräger, Germany) with an oxygen air mixture at a tidal volume of 30 to 50 ml and constant frequency of 25 $min^{-1}$. Arterial $PaCO_2$ is adjusted to about 40 mmHg by regulating the fraction of inspired oxygen ($FiO_2$) via the ratio of oxygen air mixture. Routinely the following cardiovascular and respiratory parameters are measured after placement of necessary probes and catheters fitted to appropriate pressure transducers and recording equipment: central venous pressure (via left jugular vein), arterial blood pressure and heart rate (BP and HR; via left carotid artery), left ventricular pressure (LVP; using a Millar catheter [FMI, Mod.:SPC-340S, REF: 800-2019-1, 4F] introduced into the left ventricle via right carotid artery), pulmonary arterial pressure (PAP; using ARROW Berman angiographic balloon catheter [REF.: AI-07134 4 Fr. 50 cm] placed into the pulmonary artery via left jugular vein), cardiac output (CO) and extravascular lung water index (EVWLI) by use of the PiCCO system (Pulsion, Germany) connected to a Pulsion 4F Thermodilution-catheter (PV2014L08N) placed into the right femoral artery. Catheters for measurement of CVP, BP, HR, LVP, and PAP are fitted to a Ponemah recording system. Arterial blood gas analysis is performed to determine the $PaO_2/FiO_2$. According to the American-European Consensus Conference on ARDS a $PaO_2/FiO_2<300$ mmHg is considered as indicative for the presence of acute lung injury. Dependent on the applied protocol duration of experiments varied between 4 and 5 hours after administration of lung injury inducing challenge. At the end of experimentation pigs are sacrificed by exsanguination and bronchoalveolar lavage fluid (BALF) is collected from lungs. Cellular content of BALF is determined by use of a blood cell counter (Cell DYN 3700).

In a typical setting acute lung injury is induced by intratracheal instillation of Lipopolysaccharide (LPS; *E. coli* 0111:B4; Sigma L2630) in saline at a dose of 5 mg/kg body weight into each lung via the endotracheal tube. PAP and EVWLI increased while $PaO_2/FiO_2$ decreased below 300 mmHg in response to the challenge. The cellular content of BALF is significantly increased Administration of compound 1 of this invention as i.v.-bolus 15 min before the LPS challenge ameliorated or prevented the LPS induced changes.

In an other protocol oleic acid (OA; Sigma-Aldrich, O1008) diluted with ethanol (1:1) is infused i.v. over 15 min at a final dose of 100 mg/kg body weight. Challenge with OA led to increase of PAP and EVLWI and decrease of $PaO_2/FiO_2$ below 300 mmHg Changes are ameliorated or prevented by administration of compound I of this invention 15 min before start of the OA infusion.

Doses of example 1≤30 μg/kg body weight (as referred to the peptide component) were found to be active in the described test systems.

C. EXEMPLARY EMBODIMENTS OF PHARMACEUTICAL COMPOSITIONS

The compounds according to the invention can be converted into pharmaceutical preparations in the following ways:

i.v. solution:

A compound according to the invention is dissolved at a concentration below saturation solubility in a physiologically acceptable solvent (for example buffers of pH 4 to pH 7, isotonic sodium chloride solution, glucose solution 5% and/or PEG 400 solution 30%). The solution is sterilized by filtration and filled into sterile and pyrogen-free injection containers.

s.c. solution:

A compound according to the invention is dissolved at a concentration below saturation solubility in a physiologically acceptable solvent (for example for example buffers of pH 4 to pH 7, isotonic sodium chloride solution, glucose solution 5% and/or PEG 400 solution 30%). The solution is sterilized by filtration and filled into sterile and pyrogen-free injection containers.

---

The invention claimed is:

1. A compound of the formula

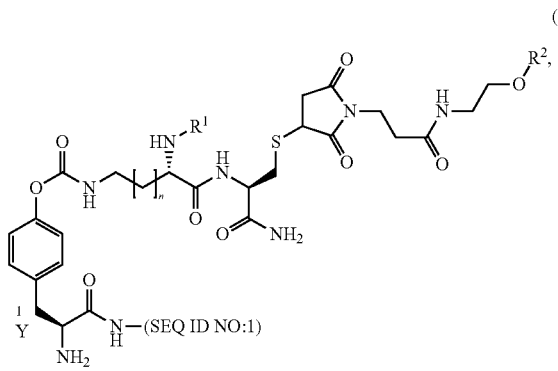

in which n represents the number 0, 1, 2 or 3,

R¹ represents hydrogen, methyl, ethyl, n-propyl or iso-propyl,

R² represents linear or branched PEG 20 kDa to 80 kDa endcapped with a methoxy-group, or a salt thereof.

2. The compound of claim 1, wherein n represents the number 1 or 2,

R¹ represents hydrogen or methyl,

R² represents linear PEG 40 kDa endcapped with a methoxy-group.

3. The compound of claim 1, wherein n represents the number 1 or 2,

R¹ represents hydrogen,

R² represents linear PEG 40 kDa endcapped with a methoxy-group.

4. A process for preparing a compound of the formula (I) or a salt thereof, as claimed in claim 1, comprising reacting a compound of formula (II)

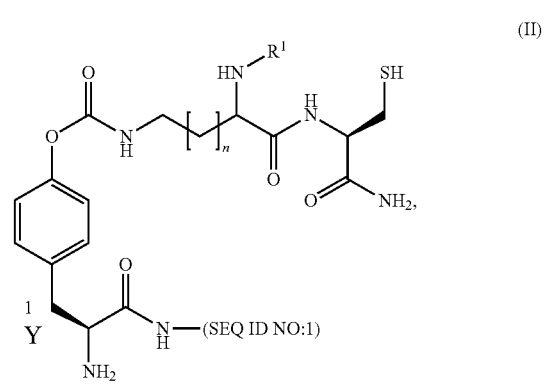

in which n and R¹ are each as defined in claim 1, with a compound of the formula (III)

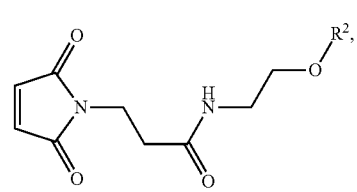

in which

R² is as defined in claim 1.

5. A method of treatment of a cardiovascular, edematous and/or inflammatory disorder comprising administering to a human or animal an active amount of a compound of claim 1.

6. A pharmaceutical composition comprising a compound as claimed in claim 1 in combination with an inert nontoxic pharmaceutically suitable excipient.

7. The pharmaceutical composition of claim 6, further comprising a further active ingredient.

8. A method of treatment of a cardiovascular, edematous and/or inflammatory disorder comprising administering to a human or animal an active amount of a pharmaceutical composition of claim 6.

9. The method of claim 8, wherein the cardiovascular, edematous and/or inflammatory disorder is selected from the group consisting of heart failure, coronary heart disease, ischemic and/or hemorrhagic stroke, hypertension, pulmonary hypertension, peripheral arterial occlusive disease, pre-eclampsia, chronic obstructive pulmonary disease, asthma, acute and/or chronic pulmonary edema, allergic alveolitis and/or pneumonitis due to inhaled organic dust and particles of fungal, actinomycetic or other origin, and/or acute chemical bronchitis, acute and/or chronic chemical pulmonary edema, neurogenic pulmonary edema, acute and/or chronic pulmonary manifestations due to radiation, acute and/or chronic interstitial lung disorders, acute lung injury/acute respiratory distress syndrome (ALI/ARDS) in adult or child including newborn, ALI/ARDS secondary to pneumonia and sepsis, aspiration pneumonia and ALI/ARDS secondary to aspiration, ALI/ARDS secondary to smoke gas inhalation, transfusion-related acute lung injury (TRALI), ALI/ARDS and/or acute pulmonary insufficiency following surgery, trauma and/or burns, and/or ventilator induced lung injury (VILI), lung injury following meconium aspiration, pulmonary fibrosis, mountain sickness, glomerulonephritis, acute kidney injury, cardiorenal syndrome, lymphedema, inflammatory bowel disease, sepsis, septic shock, systemic inflammatory response syndrome (SIRS) of non-infectious origin, inflammatory bowel disease and urticaria.

* * * * *

SEQUENCE LISTING

```
<160> NUMBER OF SEQ ID NOS: 2

<210> SEQ ID NO 1
<211> LENGTH: 51
<212> TYPE: PRT
<213> ORGANISM: Artificial Sequence
<220> FEATURE:
<223> OTHER INFORMATION: Adrenomedullin 2 - 52
<220> FEATURE:
<221> NAME/KEY: DISULFID
<222> LOCATION: (15)..(20)
<220> FEATURE:
<221> NAME/KEY: MOD_RES
<222> LOCATION: (51)..(51)
<223> OTHER INFORMATION: AMIDATION

<400> SEQUENCE: 1

Arg Gln Ser Met Asn Asn Phe Gln Gly Leu Arg Ser Phe Gly Cys Arg
1               5                   10                  15

Phe Gly Thr Cys Thr Val Gln Lys Leu Ala His Gln Ile Tyr Gln Phe
            20                  25                  30

Thr Asp Lys Asp Lys Asp Asn Val Ala Pro Arg Ser Lys Ile Ser Pro
        35                  40                  45

Gln Gly Tyr
    50
```

```
<210> SEQ ID NO 2
<211> LENGTH: 52
<212> TYPE: PRT
<213> ORGANISM: Artificial Sequence
<220> FEATURE:
<223> OTHER INFORMATION: modified Adrenomeddulin 1 - 52
<220> FEATURE:
<221> NAME/KEY: MOD_RES
<222> LOCATION: (1)..(1)
<223> OTHER INFORMATION: modified Tyrosine residue
<220> FEATURE:
<221> NAME/KEY: DISULFID
<222> LOCATION: (16)..(21)
<220> FEATURE:
<221> NAME/KEY: MOD_RES
<222> LOCATION: (52)..(52)
<223> OTHER INFORMATION: AMIDATION

<400> SEQUENCE: 2

Tyr Arg Gln Ser Met Asn Asn Phe Gln Gly Leu Arg Ser Phe Gly Cys
1               5                   10                  15
Arg Phe Gly Thr Cys Thr Val Gln Lys Leu Ala His Gln Ile Tyr Gln
                20                  25                  30
Phe Thr Asp Lys Asp Lys Asp Asn Val Ala Pro Arg Ser Lys Ile Ser
            35                  40                  45
Pro Gln Gly Tyr
    50
```